(12) United States Patent
Raybuck

(10) Patent No.: US 7,040,598 B2
(45) Date of Patent: May 9, 2006

(54) SELF-SEALING MALE CONNECTOR

(75) Inventor: John Raybuck, Los Angeles, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 44 days.

(21) Appl. No.: 10/438,702

(22) Filed: May 14, 2003

(65) Prior Publication Data

US 2004/0227120 A1 Nov. 18, 2004

(51) Int. Cl.
*F16L 37/28* (2006.01)

(52) U.S. Cl. .................................. 251/149.1
(58) Field of Classification Search .............. 251/149.1
See application file for complete search history.

(56) References Cited

U.S. PATENT DOCUMENTS

| | | | |
|---|---|---|---|
| 5,694,686 A | 12/1997 | Lopez | |
| 5,700,248 A | 12/1997 | Lopez | |
| 5,738,144 A | 4/1998 | Rogers | |
| 5,820,601 A | 10/1998 | Mayer | |
| 5,971,965 A | 10/1999 | Mayer | |
| 6,029,946 A | 2/2000 | Doyle | |
| 6,048,335 A | 4/2000 | Mayer | |
| 6,050,978 A | 4/2000 | Orr et al. | |
| 6,152,900 A | 11/2000 | Mayer | |
| 6,183,448 B1 | 2/2001 | Mayer | |
| 6,206,861 B1 | 3/2001 | Mayer | |
| 6,261,282 B1 | 7/2001 | Jepson et al. | |
| 6,325,782 B1 | 12/2001 | Lopez | |
| 6,344,033 B1 | 2/2002 | Jepson et al. | |
| 6,543,745 B1 | 4/2003 | Enerson | |
| 2003/0032940 A1 | 2/2003 | Doyle | |
| 2003/0060804 A1* | 3/2003 | Vaillancourt | ................ 604/533 |

FOREIGN PATENT DOCUMENTS

GB 2118440 A 11/1983

* cited by examiner

*Primary Examiner*—J. Casimer Jacyna
(74) *Attorney, Agent, or Firm*—Fulwider Patton LLP

(57) ABSTRACT

A self-sealing male connector having a body, a resilient boot mounted over the body, and a male thread hub. The body is formed with an elongate post that extends to the distal end. The body includes a fluid flow lumen extending from its proximal end to its distal end. At its proximal end, the body may be formed as a female Luer connector, or may be directly connected to tubing, or other arrangements. The internal fluid flow lumen extends through the post to its distal end. The body includes a first groove in which is mounted the boot. In a second groove is mounted the thread cuff. The thread cuff is used to engage a female connector and through thread action, draw in into engagement with the post. As the female connector is further engaged with eh sealed male connector, the post protrudes through the boot and into fluid communication with the female fluid flow passage thus establishing a flow path through both connectors. The boot forms a seal with the female connector when engaged and returns to seal the male connector post and fluid flow passage within disconnected from the female connector.

11 Claims, 24 Drawing Sheets

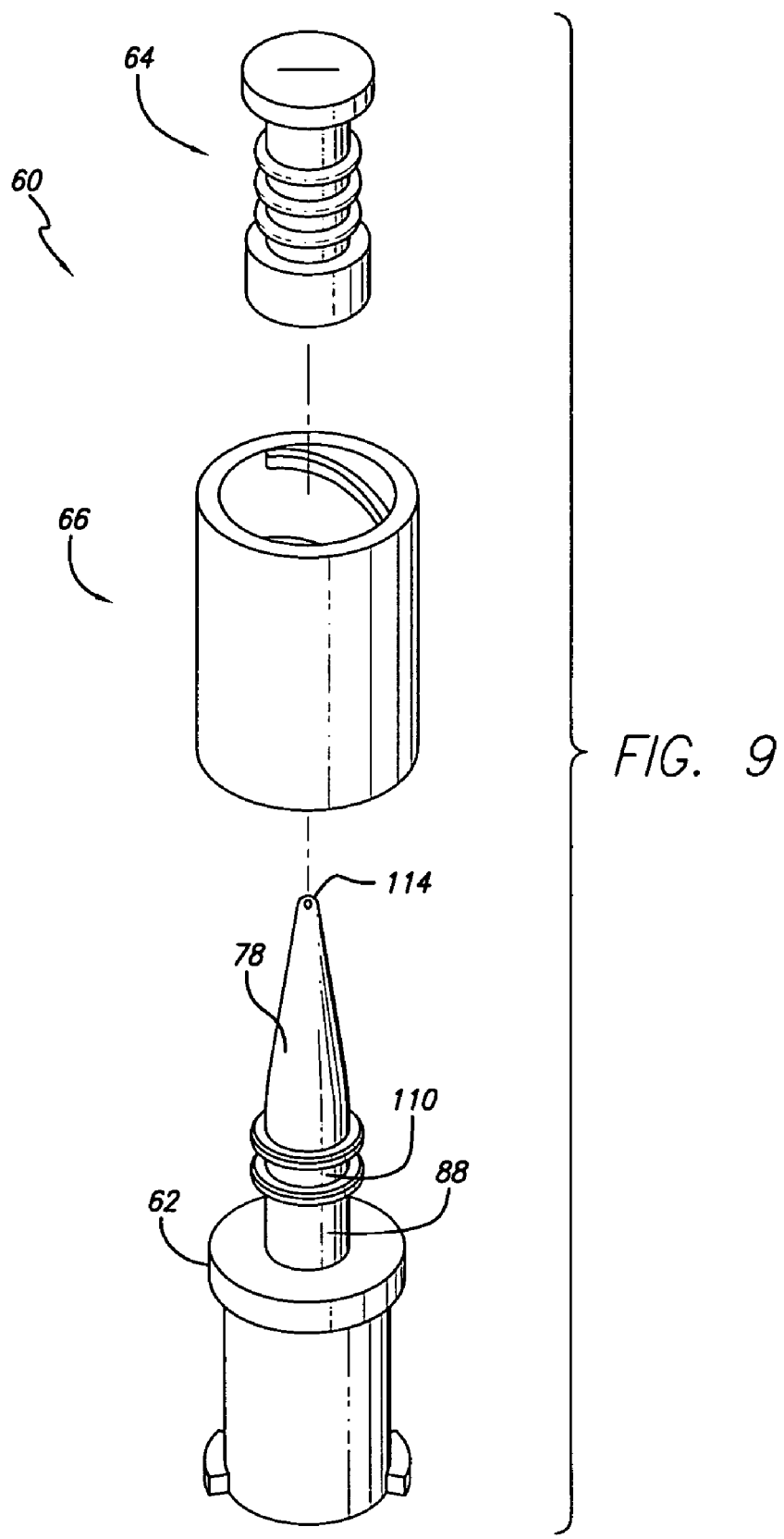

SELF-SEALING MALE CONNECTOR

BACKGROUND

The invention relates generally to medical fluid flow connectors having valves, and more particularly, to self-sealing, needle-free, male connectors.

Male and female medical fluid connectors are used in a variety of medical applications. One common application is where there is a desire to interconnect a medical device with tubing material that forms a part of a patient's intravenous ("IV") medical fluid administration set. Such administration sets typically include one or more female connectors into which may be inserted a male connector to establish fluid communication. The female connectors typically include an internal valve that is activated, or opened, by insertion of the male connector into the female connector. Once the internal valve is open, fluid may flow through both the female and male connectors in either direction. The most common types of IV fluid exchanges use a syringe fitted with a nozzle that is designed to be received into a female connector attached to the patient's IV set. The syringe may be used to infuse fluid into the patient's circulatory system or to withdraw fluid from the patient.

In the example discussed above, a common connector used for such purposes includes a Luer portion. Such connectors are well known as needle-free connectors in that no sharp objects such as sharpened needles are used for fluid conduction. In the case of female Luer connectors, a cavity is provided having a wall that tapers inward toward the center of the connector according to the generally accepted ISO Luer specification. In the case of male connectors, the male connector, or nozzle, has a taper that is complementary to the female connector taper and also meets the ISO Luer specification. The male connector is frusto-conical in general appearance.

Connectors having an integral valve that defaults to a closed position; i.e. position that prohibits fluid flow, are also known as self-sealing connectors. The integral valve may also be called a "seal". The self-sealing, needle-free connectors presently known and used in the art are generally designed to be connected to a patient's IV line, drug, or solution source, or other medical device such that the connector's seal operates to trap all fluid on the side of the connector toward the patient or other device. Such connectors are female. The typical male connector on the other hand is unsealed.

In use, the syringe or other device is often configured with a male Luer connector so as to engage the female Luer connector of the self-sealing female connector and cause the male Luer's central boss to contact the female Luer's seal membrane, opening the slit formed in the membrane and creating a fluid path through the connector. See U.S. Pat. No. 5,676,346 to Leinsing, incorporated herein by reference, for an example of a connector having a female Luer connector and an integral valve. After the necessary fluids have been dispensed or withdrawn, the syringe is removed and the slit in the needle-free connector's seal membrane closes to reseal the connector and trap all bodily fluids, including any just-dispensed medications, on the patient side of the connector.

This prevents any escape of the fluids and protects both the patient and the care giver from possible dangerous contamination. However, the free end of the syringe and any residual fluids remaining therein are unsealed and exposed. In the case of chemotherapy, some of the chemical reagents that are used are toxic and the care giver should avoid contact with them. It is more difficult to do so when the male connector is not sealed. Drops can inadvertently escape from the male connector and dwell on a flat surface where they may come into contact with the skin of a care giver, or may fall directly from the male connector to the care giver's skin. Both situations are highly undesirable.

In another case; i.e., in the area of nuclear medicine where radioactive isotopes are administered to patients, it is critical that inadvertent exposure to the isotopes be minimized for the safety of both the care giver and the patient. Such unstable elements should be carefully guarded from undesirable contact with the care giver. Yet, with the existing connectors known and used in the art, the isotope may be sealed off while still in its vial prior to administration, and may be sealed off on the patient side of the typical self-sealing female needle-free connector after administration, as discussed above, but the syringe or other device used to transfer the isotope from its container to the patient during administration is unsealed and could allow undesired exposure to the isotope.

While the self-sealing, needle-free, female Luer connectors have provided a significant advance in the art, and generally serve their intended purpose of providing a sealed, needle-free connection that remains on a patient interface or the like and allows for the connection of a syringe or other such device to dispense or extract fluids, it would be an improvement in the art if male connectors were available that also seal so that certain fluids were not allowed on exterior surfaces of syringes or other devices. Such sealed male connectors would better control exposure to fluids.

Some sealed male needle-free connectors have been known in the art; however, in some cases, numerous parts with relatively small tolerances make such connectors difficult to manufacture at a lower cost. It remains a goal of medical device manufacturers to produce high quality medical components at the lowest cost possible so that health care may reach as many people as possible.

Hence a need has been recognized by those skilled in the art for a male connector having a valve or seal that prevents leakage of fluid from the connector and during disconnection of the male connector from another connector. A need has also been recognized for a needle-free, male Luer connector that seals the male Luer connector in a male-female connection so that users of the connector are protected from hazardous drugs that remain on the Luer tip surface when disengaged. A further need has been recognized for a male connector with an integral valve that can be more easily manufactured at lower cost. The present invention fulfills these needs and others.

SUMMARY OF THE INVENTION

Briefly and in general terms, the present invention is directed to a self-sealing male connector for needle-free connection to a female connector. The female connector may form part of a patient's IV line or other such line or a container. The conventional female Luer connector is configured with a tubular body having external thread portions and a proximally-facing rim defining a fluid flow opening. An internal compressible piston may exist in the female connector.

In one aspect of the present invention, there is provided a self-sealing male connector for connection with a female connector having an opening for fluid flow in a tubular body, the tubular body having a proximal rim with a first engagement device disposed adjacent the opening, the male connector comprising a body comprising a proximal end having a proximal opening for fluid flow, an elongated post extending in a distal direction having a distal tip forming the distal end of the body and having a distal opening at the distal tip for fluid flow, the post having an outside surface, a fluid flow passage extending through the body from the proximal opening to the distal opening, the post having an outer diameter at the distal tip that is small enough to fit within the fluid flow opening of the female connector, a resilient boot mounted to the body and extending in covering relationship over the outside surface of the post to seal the distal opening of the post, and a second engagement device mounted to the body, the second engagement device adapted to interact with the first engagement device of the female connector to secure the female and male connectors together in an engaged configuration.

In other aspects, the second engagement device comprises a thread hub mounted to the body, the thread hub having internal threads for engaging threads on the exterior of the female connector. The boot is formed at its distal end with a radially outwardly flared flange, the flange having a larger diameter than the female connector fluid flow opening and having a distal facing closure wall whereby during engagement with the female connector, the rim of the female connector engages the flared flange of the boot to move the flange in the proximal direction. The flange has an opening in the closure wall located over the distal tip, wherein when the flange is moved in the proximal direction though engagement with the female connector, the distal tip protrudes through the opening of the closure wall to establish fluid flow between the male connector and the female connector. The boot's distal end is configured with a substantially planar boot flange having a distally-facing closure wall and an outside dimension greater than the inside diameter of the female connector fluid flow opening, the boot being further configured such that engagement of the first and second engagement devices brings the boot's distally-facing closure wall into contact with the female connector's rim and positions an opening of the flange substantially adjacent the female connector's opening so that as the female and male connectors are brought closer into an engagement relationship, the boot is compressed and the post tip protrudes through the opening and at least partially into the female connector's fluid flow opening.

In further aspects, the boot is formed at its distal end with a distally-tapered tip in which a boot opening is formed, the tapered tip having a smaller diameter than the female connector fluid flow opening. The boot being further configured such that engagement of the first and second engagement devices brings the boot's tapered tip into the fluid flow opening of the female connector at which location the larger diameter of the tapered end contacts the inner surface of the opening of the female connector so that as the female and male connectors are brought closer into an engagement relationship, the boot is compressed and the post tip protrudes through an opening in the boot a fluid flow is established between the male and female connectors. The boot's distal end is configured with a substantially annular, tapered boot tip having a proximal first diameter and a distal second diameter, the first diameter being larger than the inside diameter of the through-hole and the second diameter being smaller than the inside diameter of the through-hole, the boot tip being configured such that engagement of the hub with the female Luer device causes the boot tip substantially at the second diameter to enter the through-hole and contact the inside surface, thereby positioning the slit within the through-hole so that as the hub is threaded onto the female Luer device and the boot is compressed, the post tip protrudes through the slit and at least partially into the through-hole, the boot tip has substantially at its distal second diameter a distally-facing boot tip surface configured to contact the proximally-facing piston surface and, upon such contact, at least partially axially compress the piston when the boot tip is inserted into the through-hole, and post tip, upon protruding through the slit, engages the piston so as to be at least partially inserted within the diametrical opening.

In other aspects, the post tip terminates in a substantially rounded nose so as to have a nose apex, and the internal lumen intersects the nose apex with the opening being oriented in a longitudinal direction. In another approach, the internal lumen terminates proximally of the nose apex, and one or more radial cross-holes are formed in the post tip so as to communicate with the internal lumen with openings of the cross holes being oriented in a radial direction. In yet another approach, a cross-notch is formed through the post tip substantially at the nose apex so as to form opposing distally-projecting teeth at the post tip to facilitate opening a slit in the distal end of the boot and the passage of the post tip therethrough.

Further aspects include the boot being longitudinally compressible and formed at the distal end with a closure wall over the distal fluid opening, the boot having a boot opening therein for being opened by the distal tip upon compression of the boot. The body has a first groove into which is mounted the thread hub. The body has a second groove into which is mounted the boot. The thread hub is rotatably mounted to the first groove so it can rotate independently of the body whereby the body and female connector may remain rotationally stationary while being engaged together while the thread hub is rotated to fasten the female and male together. The hub is formed at a proximal end with a radially inwardly projecting annular hub flange defining an annular first hub opening, the hub flange being configured for receipt within the first groove so as to rotationally mount the hub onto the body while axially trapping the hub flange within the first groove so as to limit the hub's longitudinal movement. The first and second grooves are formed on a proximal base of the post.

Additional aspects include the post comprising a mounting groove and the boot comprises a resilient mounting lip for receipt in the mounting groove to thereby hold the boot in position on the post. The post has a proximal base and is then tapered to the distal tip wherein the proximal base has a larger diameter than the distal tip whereby the taper facilitates the boot returning to a covering relationship with the body.

The self-sealing male connector further comprises a spring configured to urge the boot to a closed position in covering relationship over the body. Further, the boot has an integral spring section formed as a part of the boot such that when the boot is compressed, the spring section urges the boot to a closed position in covering relationship over the body.

Other aspects include a self-sealing male connector for connecting to a female connector having a generally tubular barrel with external thread portions, the self-sealing male connector comprising a body having a proximal end and a distal end, the proximal end having a fluid flow opening and the distal end being configured as an elongate post extending distally of a shoulder and having a proximal post portion that is cylindrical in form and a distal post portion that is tapered to a smaller-diameter distal post tip, the proximal post portion being formed with adjacent first and second grooves, and wherein an internal lumen communicates between the proximal and distal ends, a resilient boot mounted in covering relationship about the post in the second groove, the boot being configured along a distal end with a generally diametrical slit and being further configured so as to cover the distal end of the post when the boot is in an at-rest condition, thereby restricting fluid within the internal lumen from escaping, and a male thread hub having internal threads and mounted circumferentially about the boot and the post in the first groove such that there exists nothing between the hub and boot at the distal end, whereby engagement of the hub with the female connector along the hub's internal threads and the female connector's thread portions serves to bring the distal end of the boot into contact with the female connector to thereby compress the boot, causing the post tip to protrude through the slit, and allowing fluid communication between the self-sealing male connector and the female connector through the internal lumen.

Yet further aspects in accordance with the invention include a self-sealing male connector for connecting to a female connector, the self-sealing male connector comprising a body having proximal and distal ends, the proximal end having a fluid flow opening, and the distal end being configured with a post for protruding into the female connector to establish fluid communication therewith, the post having a distal fluid flow opening, and a lumen from the proximal end to the distal end interconnecting the openings, a sealing means having an unflexed configuration for sealing the distal end of the post when mounted thereon, the sealing means being formed along at least a portion of the length, the sealing means having a compression means for allowing the sealing means to move proximally and urging it to return to its unflexed configuration, the sealing means also having an opening at its distal end that the post may open and protrude through upon the activation of the compression means, and means for connecting the male connector to the female connector to secure them in an engaged relationship.

In accordance with method aspects, there is provided a method for making a connection between male and female connectors comprising moving a sealed male connector having a tubular body with a thread hub mounted thereto and configured therein with a longitudinally projecting post having a fluid passage and terminating in a distal tip, the post being covered by the resilient boot mounted thereon, into a fluid flow opening of a female connector, engaging thread on the female connector with the thread hub so as to cause the distal end of the boot to contact the female connector rim disposed about the fluid flow opening and cause the boot to be compressed longitudinally about the post to allow the distal tip of the post to pierce the boot and project through, and fastening the male and female Luer devices together to establish a flow path between the male and female connectors.

These and other features and advantages of the present invention will become apparent from the following detailed description of the preferred embodiments which, taken in conjunction with the accompanying drawings, illustrate by way of example the principles of the invention.

BRIEF DESCRIPTION OF THE DRAWINGS

FIG. 9 is an exploded perspective view of the male connector shown in FIG. 2;

DETAILED DESCRIPTION OF THE PREFERRED EMBODIMENTS

Figure 1:
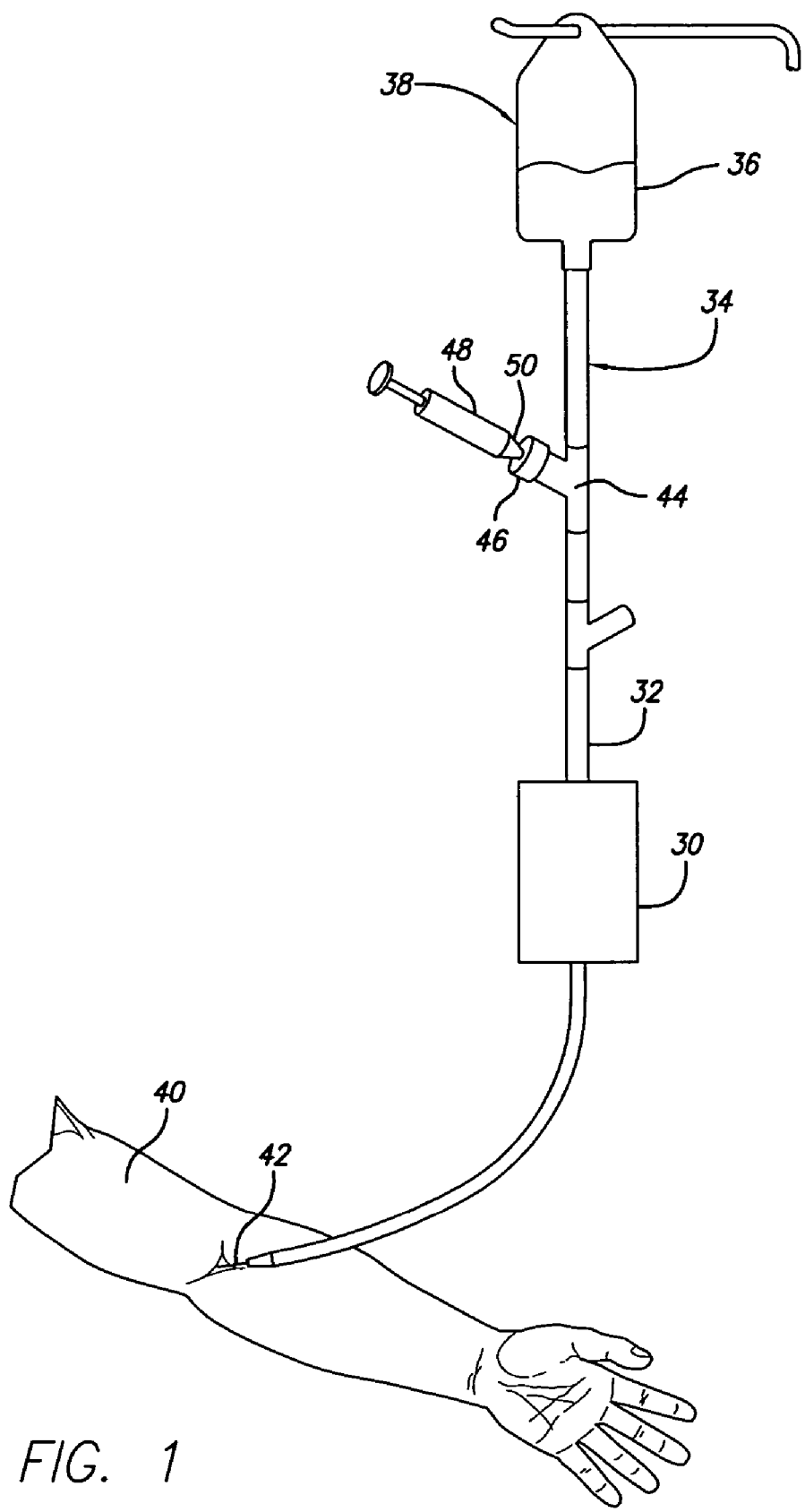
FIG. 1 is a diagram of a typical patient infusion arrangement in which an infusion pump is used to precisely control the infusion of a medical fluid from a fluid source to a patient's vessel through a medical fluid administration set having a Y-connector, the female port of the y-connector being used to infuse an additional drug by means of connecting the male Luer tip of a syringe to the Y-connector female port.

As shown in the drawings for purposes of illustration, wherein like reference numerals designate corresponding or like elements among the several views, there is shown in FIG. 1 a typical infusion arrangement. An infusion pump 30 is operating on the tubing 32 of an administration set 34 to precisely control the infusion of a medical fluid 36 from a fluid source 38, in this case a suspended bag, to a patient 40. The tubing terminates at its distal end in a cannula 42 that has been introduced to a blood vessel of the patient through which the medical fluid is infused into the patient. Mounted to the tubing is a Y-connector 44 having a female port or connector 46 comprising an integral and internal valve. This connector 46 may take the form of that shown in U.S. Pat. No. 5,676,346, referenced above. A syringe 48 having a further medical fluid has been connected with the female connector. In this case, the syringe has a male tip 50 that has been introduced to the female connector and by means of such introduction, has opened the internal valve of the female connector so that fluid communication with the tubing of the administration set may be established. The syringe may be used to either introduce fluid into the administration set from the syringe barrel or to withdraw fluid from the administration set.

Should the syringe 48 contain a chemotherapy drug that is being introduced to the patient 40, it would be undesirable for any of that drug to inadvertently fall from the syringe tip 50 as the syringe is being withdrawn from the female connector 46 of the Y-connector 44. Such drugs should not come into contact with the skin of a care giver but such a situation is possible where the male tip 50 does not have means to seal itself upon its withdrawal from the female connector.

Figure 2:
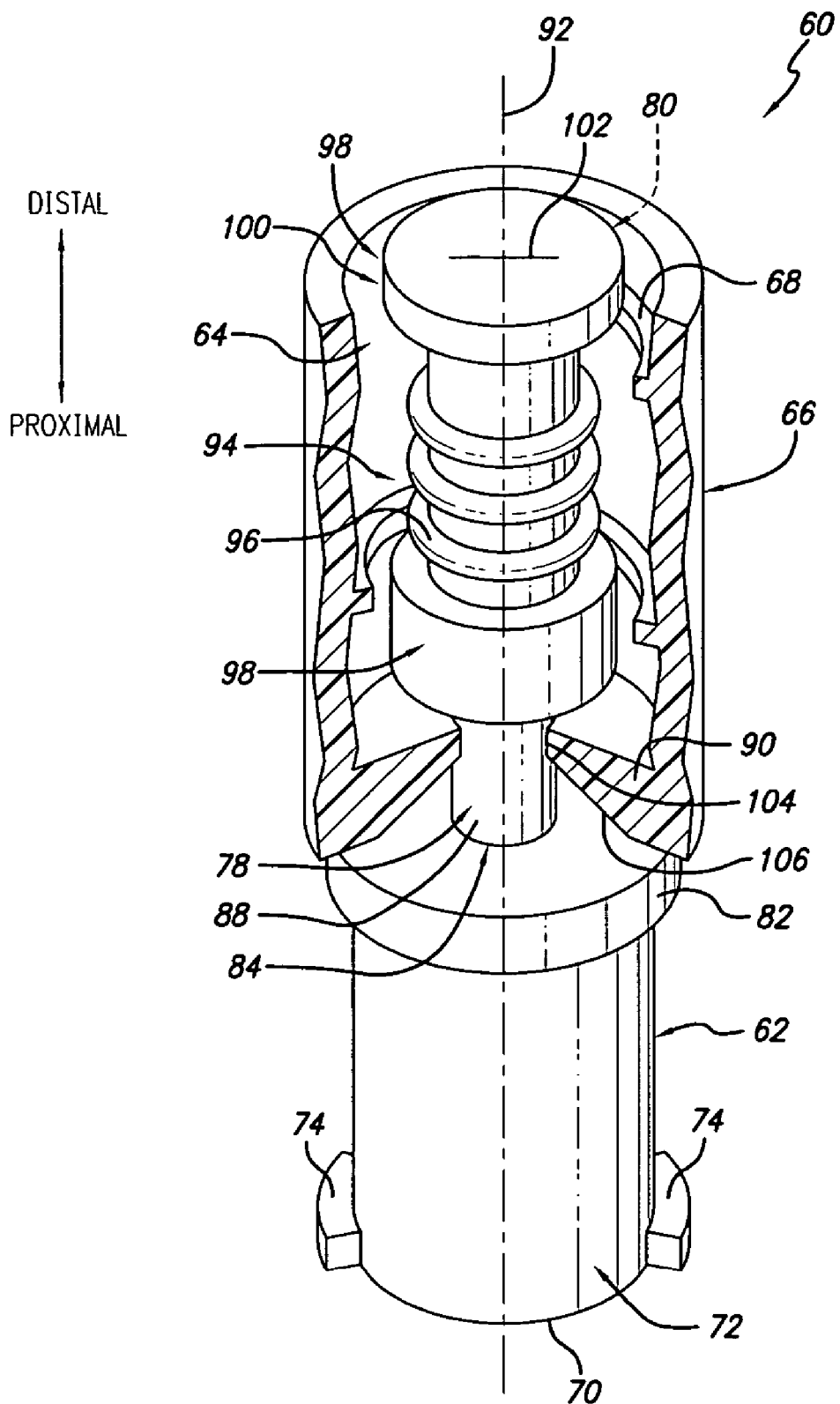
FIG. 2 is an enlarged top perspective view, partially cut away, of an embodiment of a self-sealing male connector in accordance with aspects of the present invention, the connector including a body, a resilient boot, and a male thread hub for engaging a female connector.

Referring now to FIG. 2, a cutaway perspective view from a top angle of an exemplary self-sealing male Luer connector 60 is shown. The male Luer connector has a body 62, a resilient sealing boot 64, and a male thread hub 66 having internal threads 68. The boot and the hub are seated on the body and cooperate to form a male Luer connector so as to be connected to conventional female Luer connectors known and used in the art. The proximal end of the body 70 comprises a conventional female Luer connector 72, though it will be appreciated that a variety of connectors and devices may be employed without departing from the scope of the present invention. For example, in another embodiment, the proximal end of the body may be directly connected to tubing, or it may be connected, or formed, as part of, a syringe.

As used throughout, "distal" refers to the direction toward the patient and "proximal" refers to the direction away from the patient. In this case, distal is used to indicate the end of the connector covered by the boot 64 and proximal is used to indicate the end of the connector that is female 70, in this embodiment.

Continuing with reference to FIG. 2, the female Luer connector 72 includes two thread segments 74 at the proximal end 70 of the connector body for engagement with a male thread hub. As used herein, "threads" and "thread segments" or "thread elements" are synonymous. Between the distal end 80 (not shown) of the body 62 and the proximal end 70 is a radial flange 82 having a post 78 projecting axially therefrom. The post has different shapes in different embodiments but is generally elongate and is rounded at its distal tip to form a nose, as will be shown in later figures. The base 84 of the post has a retainer flange 86

(FIG. 3) formed thereon to create a first groove 88 between it and the body flange 82. In this case, an inwardly projecting hub lip 90 is mounted within the first groove. The width of the first groove is configured to be approximately equal to or slightly larger than the width of the hub lip so that the hub is restricted in movement in the longitudinal or axial direction 92. As a matter of clarification, the longitudinal reference, or axial direction, 92 is shown in FIG. 2 and is the same throughout the figures.

Figure 3:
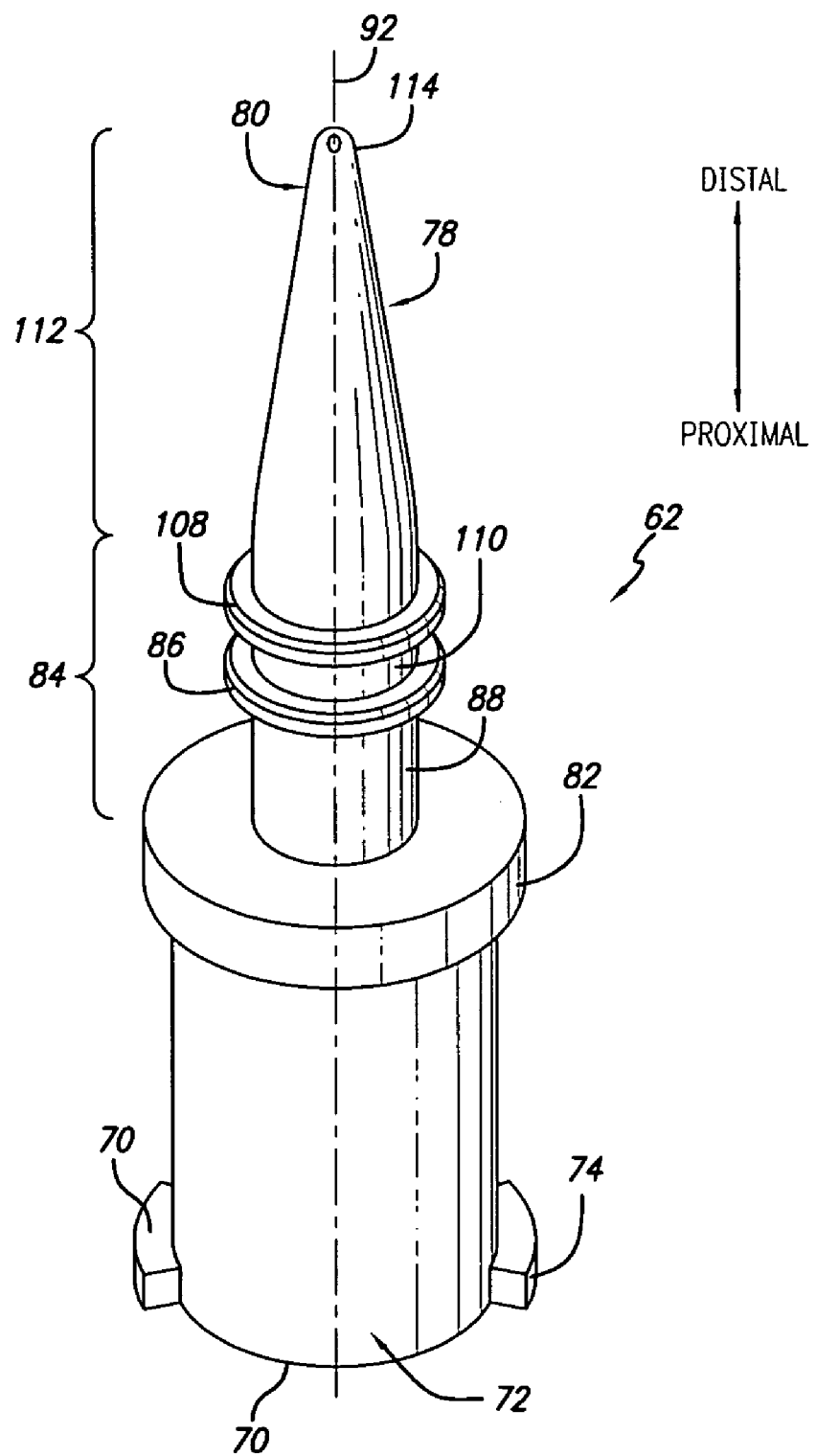
FIG. 3 is a top perspective view of the body of the male connector of FIG. 2, the body including a proximal female connector and a distal tapered post with mounting flanges along the post for retaining the other parts of the connector.

The boot 64 is received in concentric coaxial relationship about the post 78 (FIG. 3). The boot includes a central generally tubular solid wall section 94 formed along its length with axially spaced-apart annular flexible convolutions 96 that flex in accordion fashion for longitudinal collapse of the central wall section. The boot is formed with an enlarged diameter base 98 configured with a radially inwardly projecting elastic annular lip that will be shown and described below for nesting in a second groove, also shown and described below, in order to mount and secure the boot onto the post. The boot is flared radially outwardly at its distal end 98 to form an enlarged distal flange 100. The distal closure wall 98 of the boot includes a pierceable slit 102 therein.

The tubular threaded hub 66 is concentrically mounted on the body 62 substantially about the boot 64, although the boot may extend farther in the distal direction than the hub. The hub has threads 68 on its inside surface configured to engage external threads or thread portions disposed about a conventional female Luer connector. Such threads or thread elements disposed on a female Luer connector may be seen in U.S. Pat. No. 5,676,346, discussed above. The proximal hub lip 90 is somewhat flexible and its central opening 104 is large enough for receipt within the first groove 88 formed on the body 62. The hub lip is formed on its underside with a chamfer 106 that slopes inwardly in the distal direction to facilitate installation of the hub onto the body over the retainer flange (shown below) to complete the assembly of the thread hub to the body.

Referring now to FIG. 3, a top perspective view of the body 62 is shown. The body has a proximal end 70 configured as a female connector 72 with external thread portions 74. In this configuration, the proximal end may accept the male nozzle and the thread hub of a syringe and thereby adapt the syringe to the sealed male connector of the invention, as shown in FIG. 1. The body also has a distal end 80 and between the proximal and distal ends is a radial body flange 82. The elongate post 78 extends distally from the body flange and is substantially centered thereon.

The body post 78 has a post base 84 that is generally cylindrical in this embodiment. A first retainer flange 86 is formed circumferentially about the post base and is spaced in the distal direction from the body flange 82. This forms a first retainer groove 88, as was discussed in relation to FIG. 2. In that figure, the thread hub 66 is mounted and retained in the first groove. In particular, the hub lip 90 was mounted within the groove. In one embodiment, the length of the first groove exceeded the width of the hub lip so that the hub was able to move in the longitudinal direction somewhat, although it was nevertheless contained. Also, the diameter of the groove was selected so that the threaded hub may freely rotate about the post.

A second post flange 108 is formed circumferentially about the post base 84 at a position that is distal to the first flange 86 which thereby forms a second groove 110 about the post. Into this second groove is mounted the boot 64, although not shown in this figure. As will be shown in detail in a later drawing, the boot 64 likewise includes an annular mounting lip with an opening used to be placed into the second groove for mounting purposes. Thus these two grooves 88 and 110 serve to accurately locate the threaded hub and the sealing boot on the body. Due to their particular geometries and arrangements, assembly of the sealed male connector is facilitated, includes a relatively small number of parts, and may be manufactured at lower cost.

It should be noted that in the embodiment shown, the first and second grooves are made by forming flanges on the post that effectively result in "grooves" between them. However, other techniques may be used to form grooves. For example, the base of the post may be formed with a much enlarged outer diameter and undercuts are made in the material to form the first and second grooves. Also, in this embodiment, the grooves are referred to as being formed on the post; however, the post is part of the body in this embodiment and the grooves may be formed on other parts of the body, as will be shown in a later figure.

With continued reference to FIG. 3, the post 78 is tapered 112 along its length from a larger diameter at the base 84 to a smaller diameter at its distal tip 114. In the case shown in FIG. 3, the distal tip of the post is generally rounded. It has been found that the rounded tip 114 assists in piercing the slit of the boot (FIG. 2). Additionally, this taper feature of the post has been found to be beneficial in that it tends to urge the outer boot 64 towards the closed position, shown in FIG. 2. That is, when the boot has been moved in the proximal direction over the post due to engagement of the sealed male connector with a female connector, the open slit of the boot will have moved to a position along the tapered section of the post. Because the taper is towards a smaller diameter in the distal direction, and the boot is formed of resilient material that is self-biased to return to its closed and sealed configuration; i.e., the sealed configuration shown in FIG. 2, the taper of the post will assist the boot in sliding towards that sealed configuration.

Figure 4A:
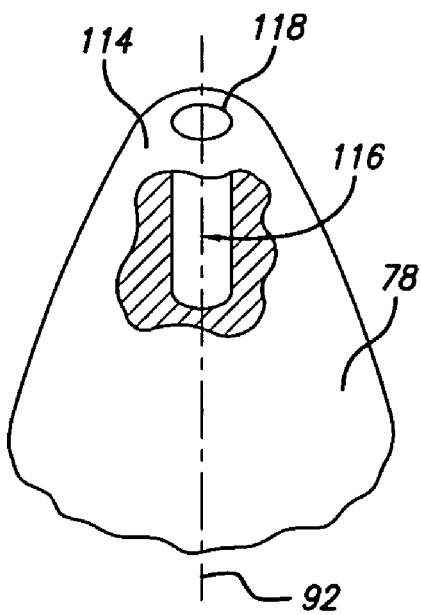
FIG. 4a is an enlarged top perspective view, partially cut away, of the distal tip of the post of the body shown in FIG. 3 showing the internal fluid lumen and a distal tip opening for that lumen.

Turning now to FIG. 4a, an enlarged top perspective view of the post 78 distal tip 114 is shown partially in section. A central longitudinal internal lumen 116 is formed substantially along the longitudinal axis 92 of the post. In this embodiment, the lumen intersects the apex of the post tip so that a hole or opening 118 is formed substantially centered on the tip, is longitudinally oriented, and allows for fluid communication through the tip to the internal lumen. Moreover, it will be appreciated by those skilled in the art that the size of the post and its lumen may be such that the opening 118 can engage and center on the tip of an internal post or spike formed in prior art self-sealing female Luer connectors (not shown).

Figure 4B:
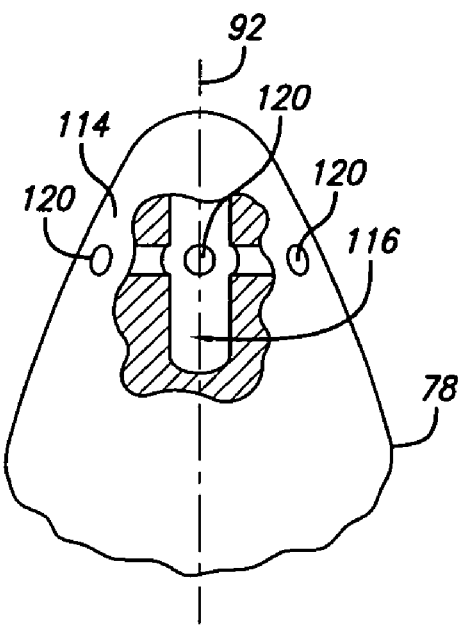
FIG. 4b is also an enlarged top perspective view, partially cut away, of the distal tip of the post of the body shown in FIG. 3 showing the internal fluid lumen and an alternative arrangement of openings leading to and from the internal lumen.

An alternative embodiment of the distal tip 114 of the post 78 is shown in the enlarged top perspective view of FIG. 4b, partially in section. The post tip is again generally rounded and the post includes the longitudinal internal lumen 116. However, unlike the embodiment shown in FIG. 4a, the lumen does not intersect the apex of the tip but terminates proximally of the apex within the post tip. Cross-holes 120 are formed in the post tip generally radially to the longitudinal axis 92 to join with the central lumen. The inside diameter of the individual cross-holes may be smaller than that of the internal lumen, but with three such cross-holes as shown in FIG. 4b, the total cross-sectional area of the fluid flow paths created by the cross-holes is equal to or greater than the cross-sectional area of the internal lumen so that the cross-holes will not be an impediment to the communication of fluid through the internal lumen. It will be appreciated by those skilled in the art that other numbers and sizes of cross-holes are possible to achieve the desired flow characteristics. By providing multiple holes in the post tip and positioning the holes radially about the nose it will be further appreciated that the likelihood that the flow path will become occluded is reduced.

Where the male connector device of the present invention is connected to a prior art self-sealing female connector having an internal spike that is fluted with transverse passages leading to a proximal bore (not shown), rather than having a central through-hole, the blunt nose of the alternative embodiment post shown in FIG. 4b can engage the spike while a fluid flow path is created between the cross-holes and the transverse passages of the female spike, unobstructed by the engagement of the blunt nose with the spike tip.

Figure 4C:
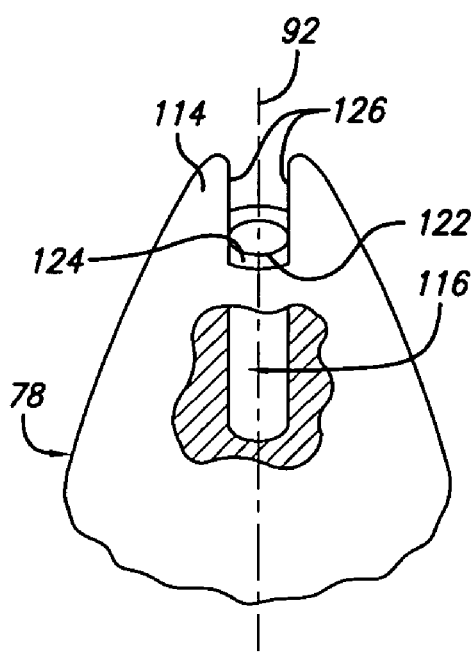
FIG. 4c is yet another enlarged top perspective view, partially cut away, of the distal tip of the post of the body shown in FIG. 3 showing the internal fluid lumen and another alternative arrangement of openings leading to and from the internal lumen in which a lateral slot has been formed in the distal tip.

Another alternative embodiment of the post 78 is shown in the enlarged top perspective view of FIG. 4c, partially in section. The post tip 114 is again generally rounded with the internal lumen 116 that intersects the tip apex to form an opening 122, much like the embodiment of FIG. 4a. In addition, a transverse cross-notch 124 is formed cross-wise through the apex of the tip in a direction perpendicular to the longitudinal axis 92. The cross-notch 124 may have a width substantially equivalent to the diameter of the internal lumen 116 so that the remaining portions of the rounded nose left standing on opposite sides of the notch form distally protruding teeth 126 about the opening 122. The teeth facilitate the passage of the post tip through the slit 102 in the boot 64, as will be shown below and prevent any sealing surfaces that may exist in the female mating connectors and other larger objects that may be within the fluid system from laying flush over the opening 122 and blocking flow through the opening. Thus, the cross-notch cooperates with the lumen to allow fluid to flow through the end of the tip both coaxially and laterally, thereby reducing the likelihood that the opening will become occluded.

It will be appreciated by those skilled in the art that a variety of other post tip configurations may be employed in optimally engaging now known and later developed female connectors without departing from the spirit and scope of the invention.

Figure 5:
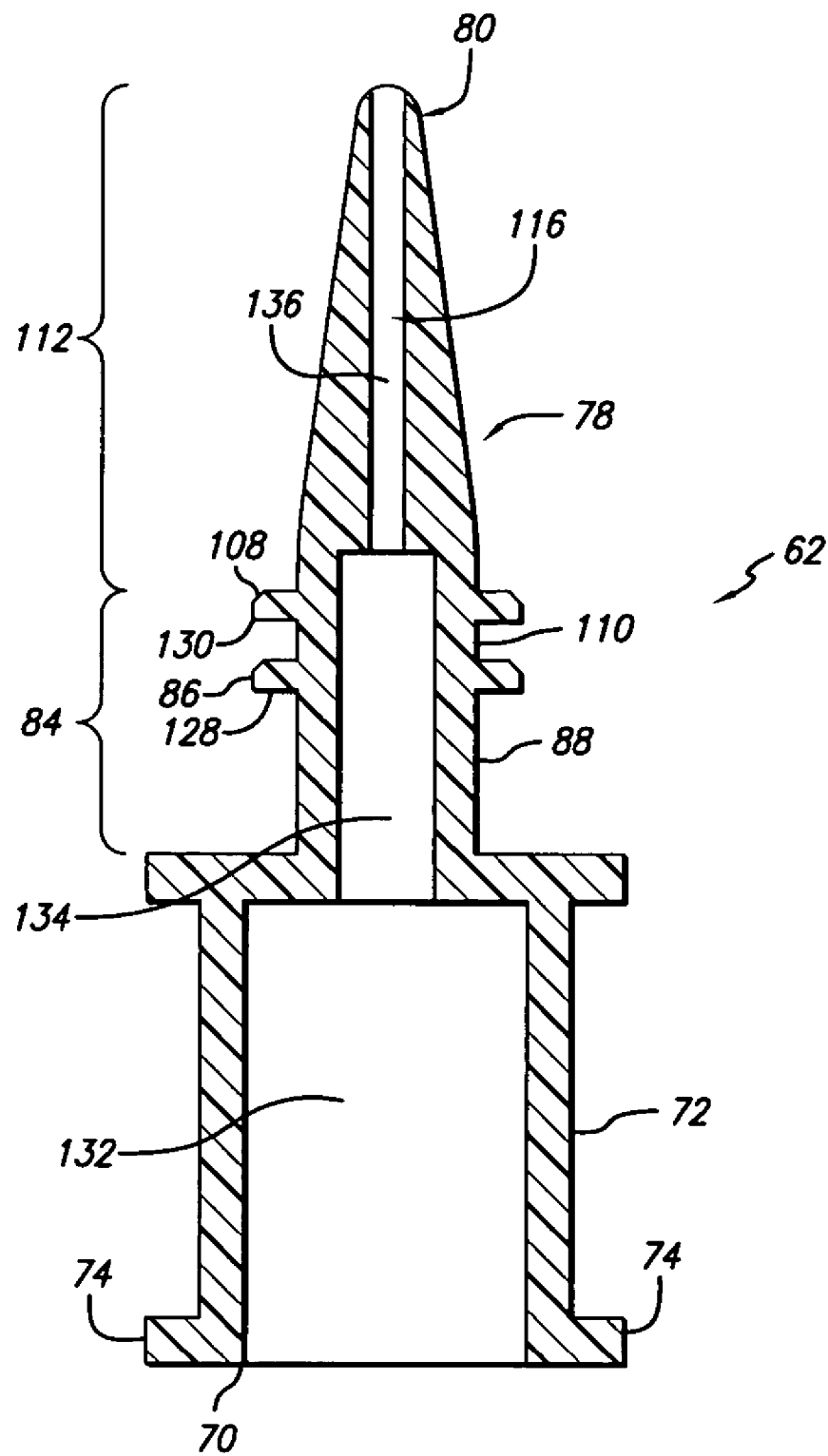
FIG. 5 is a front cross-sectional view of the body shown in FIG. 3 of a male connector in accordance with aspects of the invention.

Turning now to FIG. 5, a side, cross-sectional view is seen of the body 62 shown in the perspective views of FIGS. 2 and 3. The first and second annular flanges 86 and 108 located on the base 84 of the post 78 are formed with a ramp profile to facilitate moving the thread hub and the boot over them for assembly in their respective grooves 88 and 110. In this case, the ramp, or chamfer, or radiused edge is located on the distal sides of the flanges. In another embodiment, the flanges may be square to provide well-defined edges for the retention of the corresponding mounting surfaces of the boot 64 and the thread hub 66, which is particularly significant regarding the proximal edges 128 and 130 of the first and second flanges respectively. While the flanges are shown as being of generally equal diameter in FIG. 5, it will be appreciated that the second flange 108 may have a smaller diameter than that of the first 86 so that the thread hub 66 may more easily clear the second flange and is only snap-fit over the first flange to seat on the body.

As also shown in FIG. 5, the body's internal lumen 116 comprises stepped diameter sections 132, 134, and 136. The proximal lumen section 132 has the largest inside diameter and has an internal taper to form a female Luer connector 72. The middle lumen section 134 has a smaller inside diameter located within the base 84 of the post. The distal lumen section 136 has the smallest inside diameter located within the tapered portion 112 of the post. The proximal and middle lumen sections are shown as terminating in square bottoms on which the next respective stepped lumen section is centered. The bottoms of the respective lumen sections may also be formed with angled or filleted edges. It will be appreciated that various stepped lumen configurations may be provided within the body so as to achieve the desired wall thickness and the necessary size of the fluid flow path from the body's proximal end 70 to its distal end 80.

It will be appreciated by those skilled in the art that the configuration of the body 40 shown in FIGS. 2, 3, and 5 is well-suited for the injection molding manufacturing process, whereby the body may be made in a relatively simple two-half mold cavity with a single linear core pull. The distal tip 80 configuration with cross-holes shown in FIG. 4b may require the use of additional mold core pins on separate slides. Because the design of the body is particularly suited to injection molding, then, it may be formed from a variety of plastic materials such as polyethylene, polypropylene, polycarbonate, PVC, ABS, acrylic, and K-resin. Further, the body may also be formed in a metal injection molding ("MIM") process from materials such as aluminum, magnesium, glass, nylon and polycarbonate. Other materials and molding or forming processes may also be possible without departing from the scope of the invention.

Figure 6:
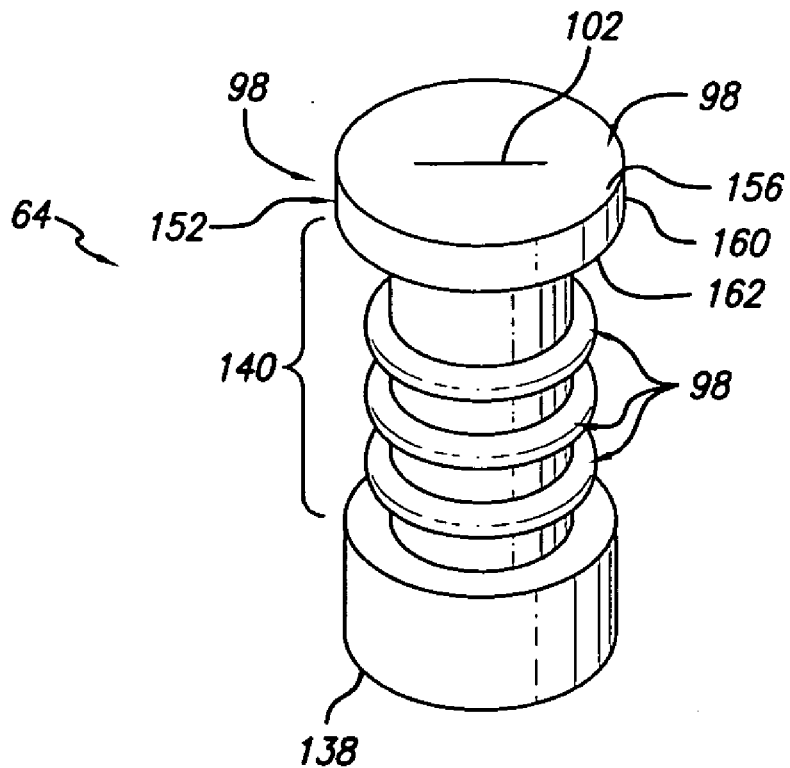
FIG. 6 is a top perspective view of the boot shown in FIG. 2 of the male connector in accordance with aspects of the invention, the boot including a proximal lip, a distal flange, and an intermediate spring section.
Figure 7:
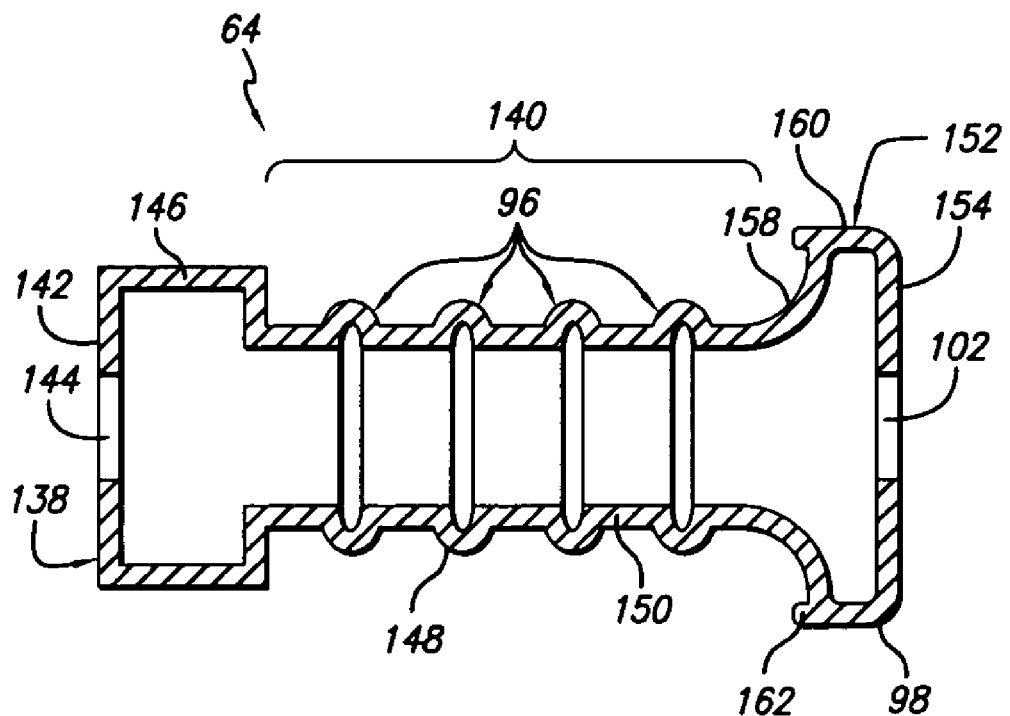
FIG. 7 is a front cross-sectional view of the boot shown in FIG. 6.

Referring now to FIGS. 6 and 7, views of the boot 64 are presented. In FIG. 6, a top perspective view of the resilient boot is shown and in FIG. 7, a side cross-sectional view is presented. The boot generally has a proximal end 138 configured to be mounted within the second groove 110 on the post 78 (FIG. 3) and a distal end 98 configured with a slit 102. In the exemplary embodiment shown, between the proximal and distal ends of the boot there are formed a number of parallel, adjacent circumferential ribs or convolutions 96 that together form an axially compressible spring section 140.

The boot 64 is formed at its proximal end 138 with an annular lip 142 defining an axially disposed circular opening 144. The lip is configured with the opening having an inside diameter selected to closely fit the outside diameter of the base 84 of the post 78 within the second groove 110 (FIG. 3) and a thickness of less than or equal to the width of the second groove so that the boot lip may be firmly mounted in the groove. The lip terminates radially outwardly at a proximal side wall 146 that has an inner diameter large enough to clear the post's second flange 108. The proximal side wall of the boot then turns radially inwardly again to transition to the middle ribbed spring section 140.

The spring section 140 of the resilient boot 64 is formed in one exemplary embodiment with four parallel, adjacent circumferential ribs 96 that form convolutions. The ribs consist of radially outwardly extending arcuate sections 148 formed in spaced apart relationship about the boot's mid-section. The arcuate sections are substantially equidistant and interconnected by linear sections 150 so as to form the integral compressible spring along the midsection of the boot's length. The spring section is configured having a substantially constant wall thickness including the arcuate and linear sections. In this way, when the boot is compressed during use of the self-sealing male connector 30, the arcuate sections can close and the linear sections can flex, thereby allowing the overall length of the boot to be reduced substantially while generally maintaining the boot's axial alignment.

It will be appreciated that the number and size of the ribs may be varied to achieve the axially compressible spring section of the boot. Moreover, it will be further appreciated that while the compressible section is described and shown as a spring having circumferential ribs, various other configurations allowing axial compression, such as an accordion-type construction, conically-shaped walls converging inwardly from the opposite ends, folded or rolled walls, flexible lengthwise ribs or pleats, telescoping axial sections, helically flexing sections, or a compressible foam material, may be employed in the present invention. Other forms of a spring may be used that bias the boot to a desired location. For example, a separate coil spring of a suitable material may be fashioned to bias the boot to the distal end of the connector. The flow path through the body shown in FIG. 2 is through a lumen that is internal to the post and thus the spring would be considered to be external to the fluid path.

The distal end of the spring section 140 of the boot 64 transitions to the distal end 98 of the boot comprising an enlarged boot flange 152 having a distally-facing closure wall 156 in which is formed the diametrical slit 102. The pierceable slit 102 may be configured in a number of different forms or shapes, such as cruciform slits, overlapping flaps, deflectable edges or any other construction known to those skilled in the art or which might be developed in the future.

The distal boot flange 152 also includes a proximal surface 158 (FIG. 7) interconnected with the distal closure wall 156 by an annular side wall 160. The proximal surface 158 includes at its periphery a proximally-projecting annular lip 162 used to provide integrity and stability to the boot flange and to help maintain its generally planar shape even when the boot is compressed.

As with the body 62 (FIG. 3), the resilient boot 64 is also susceptible to being manufactured through a molding process. The slit 102 and the proximal opening 144 may be formed in a secondary operation. A plastic material from a flexible, medical-grade polymer family such as polyurethane, silicone, Kraton®, thermoplastic elastomers, and rubber may be used.

Figure 8:
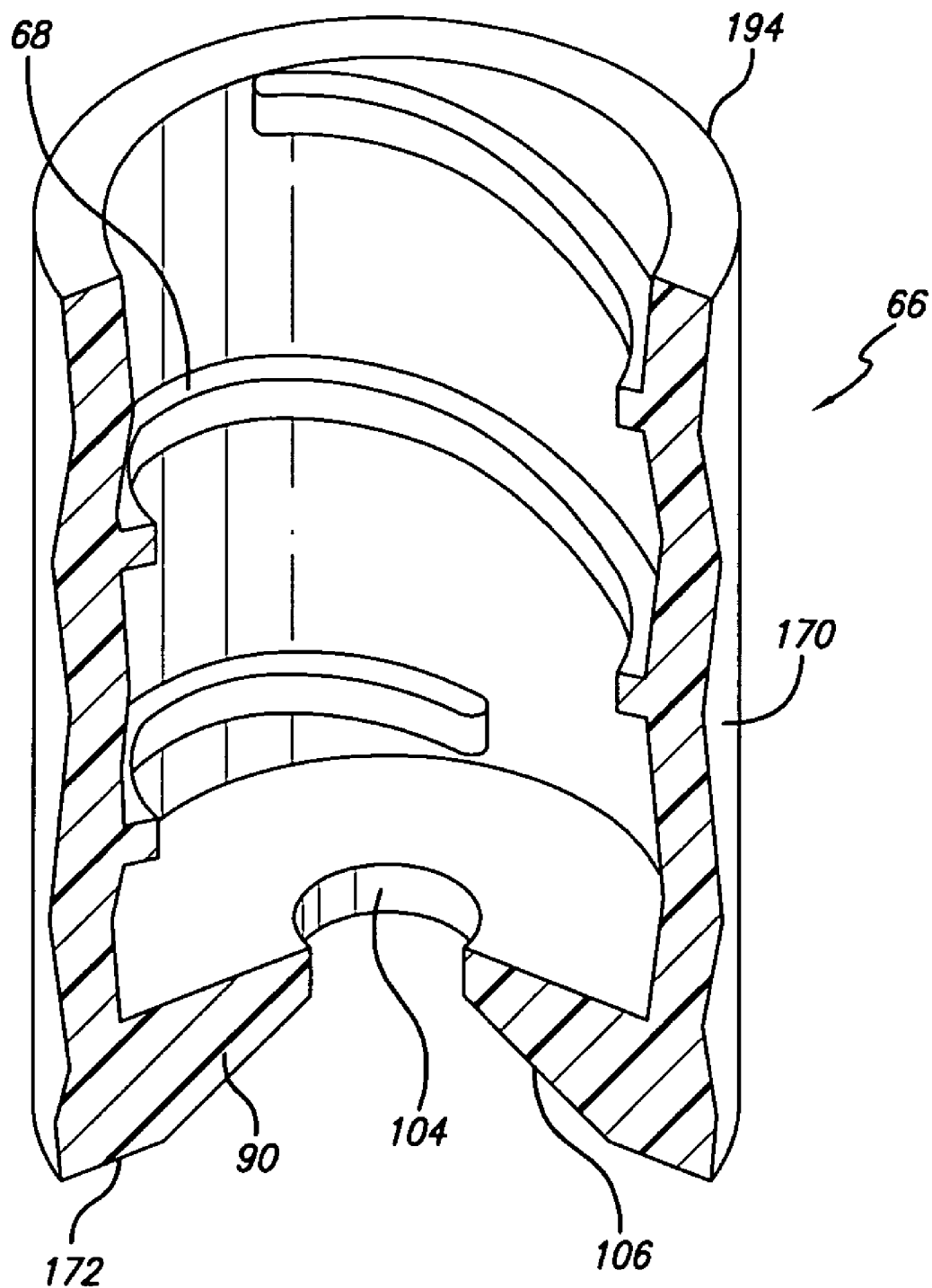
FIG. 8 is a top perspective view, partially cut away, of the hub of the male connector shown in FIG. 2 revealing a proximal mounting lip and internal threads for engaging the external threads of a female connector.

In FIG. 8 there is shown a top perspective view, partially cut away, of the male thread hub 66 shown in FIG. 2. The hub is generally cylindrical with a side wall 170 and a proximal end wall 90 or lip at the proximal end 172 of the hub. The distal end 174 is open. The inside surface of the annular side wall includes threads 68 capable of engaging threads or thread elements located on a female connector, in this embodiment. Standard threads for Luer connectors may be used, or other arrangements. The proximal lip of the thread hub includes a central opening 104 configured to be received within the first groove 88 on the base 84 of the post 78 (FIG. 3). As such, the inside diameter of the hub's opening 104 is slightly larger than the outside diameter of the first groove but smaller than the outside diameter of the radial flange 82 of the body, and smaller than the outside diameter of the first flange 86 located on the post. Once the hub has been passed over the post 78 (FIG. 3) and has been seated in the first retaining groove 88, the first flange 86 limits movement of the hub in the distal direction while the radial body flange 82 limits movement of the hub in the proximal direction. The distance between the first flange 86 and the radial body flange 82 is typically larger than the thickness of the hub lip 90 thereby allowing the hub to have some freedom of movement in the longitudinal direction. As a result of this configuration, the hub is free to rotate about the post but is restricted in its longitudinal movement along the post.

With continued reference to FIG. 8, in order to facilitate mounting the thread hub 66 onto the post 78 (FIG. 3) the proximal lip 90 is ramped or chamfered to form a circumferential angled surface 106 leading inwardly to the opening and enabling a snap-fit of the hub as it is installed proximally onto the post. It will be appreciated by those skilled in the art that the lip 90 may also be configured with radial slits or a circumferential groove (not shown) to form a more flexible, living hinge-type lip to further facilitate assembly of the hub onto the body. Longitudinal ribs or knurled features (not shown) may be formed on outside of the side wall 170 to better enable grasping and rotating the hub during use. It will be appreciated that all such features, along with the overall hub design, make the hub well-suited to an injection molding manufacturing method using such plastic materials as polyethylene, polypropylene, polycarbonate, PVC, ABS, acrylic and K-resin. It will be further appreciated that though the hub is shown and described as being configured to be rotatably mounted on the body, the hub may also be non-rotatably mounted on the body, permanently mounted on the body as through a solvent bonding or ultrasonic welding process, molded in a single step with the body or in a subsequent step over the body, or may be otherwise formed integrally with the body.

Although a thread hub is described herein and shown in the figures, other means of securing the engagement of the female connector to the male connector may be useful. For example, a clip arm or arms on either of the connectors with slots or protrusions on the other connector may work just as well. Other securing arrangements may occur to those skilled in the art.

Referring now to FIG. 9, there is seen an exploded perspective view of the self-sealing male connector 60 shown in FIG. 2 indicating an assembly of the hub 66 and the boot 64 onto the body 62. Firstly, the hub is mounted on the post 78 by pressing the hub over the post and snapping the hub proximal opening into the first retaining groove 88. Secondly, the boot is mounted on the post by moving the boot over the post until the boot proximal opening 144 (FIG. 7) engages the second retaining groove 110 so that the boot protrudes axially out of the center of the hub and completely encloses the post tip 114. As such, with these two simple assembly steps involving three components, the self-sealing male connector in accordance with aspects of the present invention is complete and fully operable.

Figure 10A:
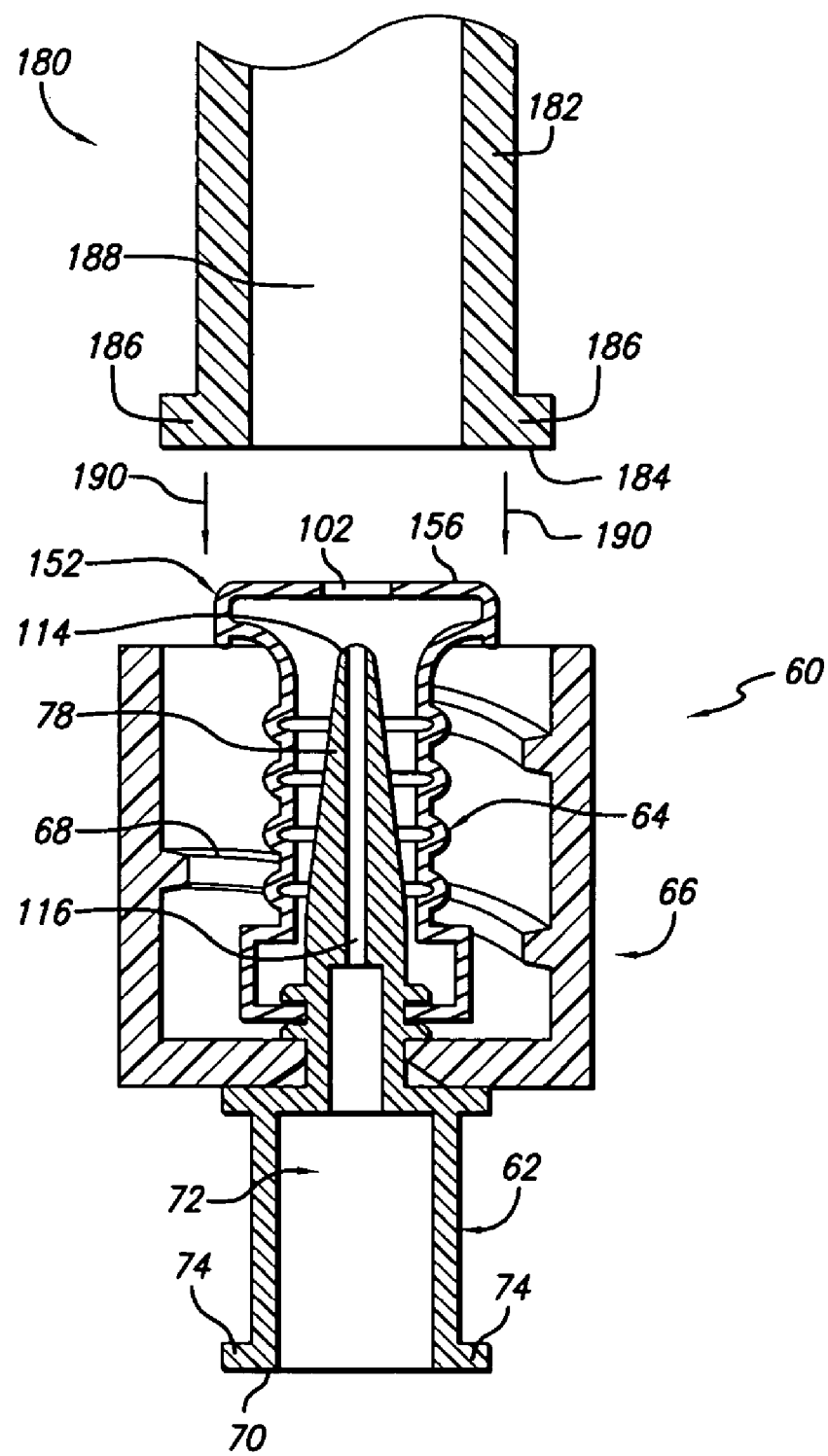
FIG. 10a is a front cross-sectional view of the sealed male connector shown in FIG. 2 further showing a cross-sectional view of an adjacent conventional female Luer connector in position to engage the male connector, showing the boot flange of the male connector to be larger than the opening of the fluid flow passage of the female connector.

Turning now to FIG. 10a, there is shown a cross-sectional view of the assembled self-sealing male connector 60 of FIG. 2 about to engage a female connector 180, depicted in section. The female connector has a generally tubular body 182 forming a barrel configuration with a proximal rim 184 and external female thread portions 186. The connector includes a longitudinal fluid flow passage 188 centered on the proximal rim. Although not shown, the self-sealing male connector 60 may be attached to a syringe 48 (FIG. 1) or other dispenser or fluid device at its proximal end 70 that is to be connected to the female connector 180 of a patient's IV line 34 (FIG. 1) or a solution dispenser. The female connector 180 is next moved toward the male connector 60 or vice versa, in the direction of the arrows 190. In doing so, the proximal rim of the female connector will be brought into contact with the large closure wall 156 of the distal flange 152 of the boot 64. The outside diameter of the boot distal flange 152 is greater than the diameter of the female connector's fluid passage 188 and consequently, the proximal rim 184 of the female connector will make contact with the boot distal flange closure wall 156.

Thus, with the proximally-facing rim 184 of the female connector 180 facing the male connector's 60 distal flange 152, further proximal movement of the female connector as to engage the external female thread portions 186 with the internal threads 68 of the hub 66 will serve to bring the female rim and the male distal flange into contact and compress the boot causing the tip 114 of the post 78 to partially protrude through the slit 102 formed in the boot's distal end.

Figure 10B:
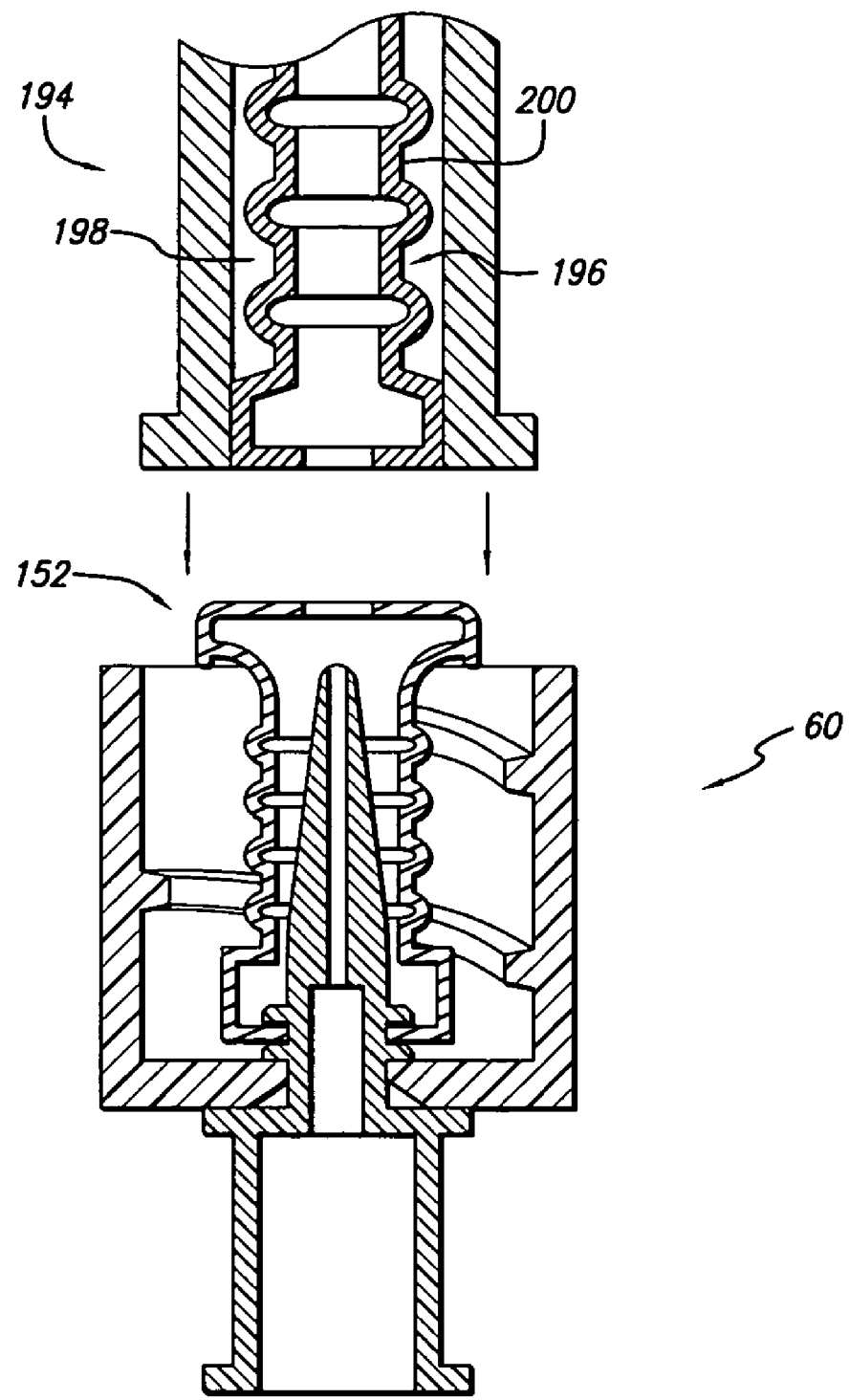
FIG. 10b is a front cross-sectional view of the sealed male connector shown in FIG. 2 further showing a cross-sectional view of an adjacent conventional female Luer connector having an internal sealing piston, in position to engage the male connector, showing the boot flange of the male connector to be larger than the opening of the fluid flow passage of the female connector.

Referring briefly to FIG. 10*b*, a similar arrangement to FIG. 10*a* will be seen except that the female connector 194 has an internal sealing device or valve 196 located in the fluid passage 198 of the female connector. The female connector valve comprises a compressible internal piston 200 making the female connector also self-sealing.

As is known in the medical field, syringes and other medical dispensing devices used in administering and withdrawing medicinal solutions or bodily fluids typically employ a conventional male Luer connector. In an embodiment in accordance with the present invention, the self-sealing male connector 60 is configured to accept and work with female Luer devices such as that shown in FIGS. 10*a* and 10*b*. The size of the thread hub 66 and its threads 68 are configured to secure a standard female Luer device. The size of the post 78 is selected to fit within the fluid passage of a standard female Luer connector and the size of the distal flange 152 of the boot is selected so as to be larger than the fluid passage 188 of a standard female Luer device. The proximal end 70 of the body 62 of the male connector 60 has female thread portions 74 so that it can be conveniently and easily attached to a male Luer connector (not shown) on a syringe or other device. As such, the male connector 60 in accordance with the invention performs the function of the male Luer connector of the syringe itself when the device is attached thereto. Thus, a self-sealing male connector in accordance with the present invention adapts the conventional, unsealed male Luer connector of a syringe to a desirable self-sealing male Luer connector.

It will be appreciated that when the boot 64 is in its at-rest configuration with the slit 102 closed as shown in FIG. 2, the post 78 is completely encapsulated within the boot. Therefore, when the self-sealing male connector 60 is connected at its proximal female connector end 70 to a male Luer connector on a syringe, any fluids within the post's internal lumen 116 on the syringe side of the post will be sealed off by the boot and not allowed to escape from the syringe. In this way, when the self-sealing male Luer device is operably connected to a syringe or other such device it serves to allow the syringe to interface with female Luer connectors as before while preventing the escape of any fluids from the syringe when the syringe is not connected to the female Luer connector thereby providing for the effective, safe, and contamination-free administration of fluids through a syringe or the like. No sharp needle is required to interface with the self-sealing male connector in accordance with the invention thereby further preventing risk of cross-contamination through inadvertent needle punctures of the patient or care giver.

Figure 11A:
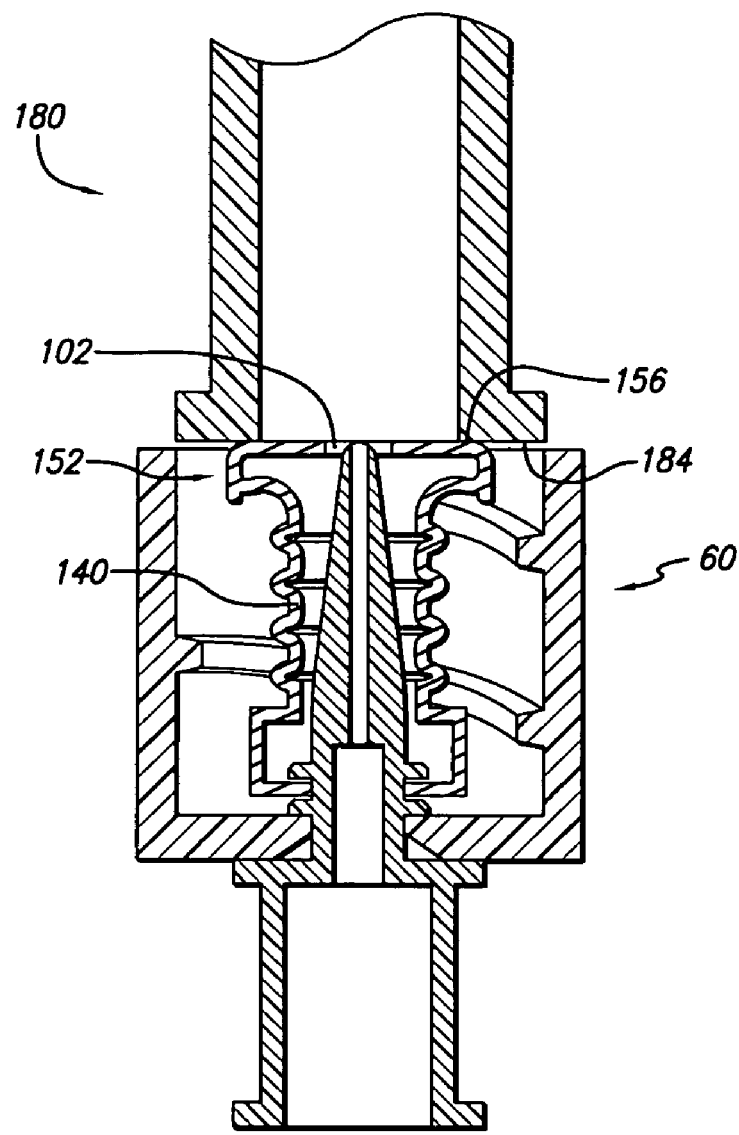
FIG. 11a is a front cross-sectional view of the male connector of FIG. 10a beginning engagement with the female Luer connector also shown in FIG. 10a, wherein the rim of the female connector has begun compressing the boot so that the distal tip of the male connector post begins protruding through the boot to establish a fluid flow path.
Figure 12:
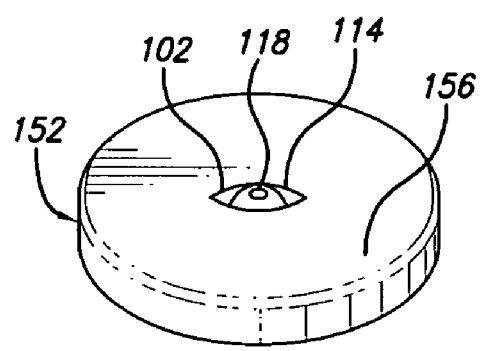
FIG. 12 is a partial top perspective view of the post of the male connector protruding through the slit in the boot with the lumen of the post now able to establish fluid flow outside the male connector.

Referring now to FIG. 11*a*, the female Luer connector 180 has been advanced proximally toward the self-sealing male Luer device 60 so as to bring the female Luer device's proximal rim 184 into contact with the distal closure wall 156 of the boot's distal flange 152. It can be seen that the spring 140 of the boot is slightly compressed and the distal tip 114 of the post is beginning to protrude through the slit 102 formed in the boot's distally-facing surface. FIG. 12 is a top perspective view showing just the distal tip 114 of the post with its fluid flow opening 118 protruding through the distal closure wall 156 of the distal boot flange 152.

Figure 11B:
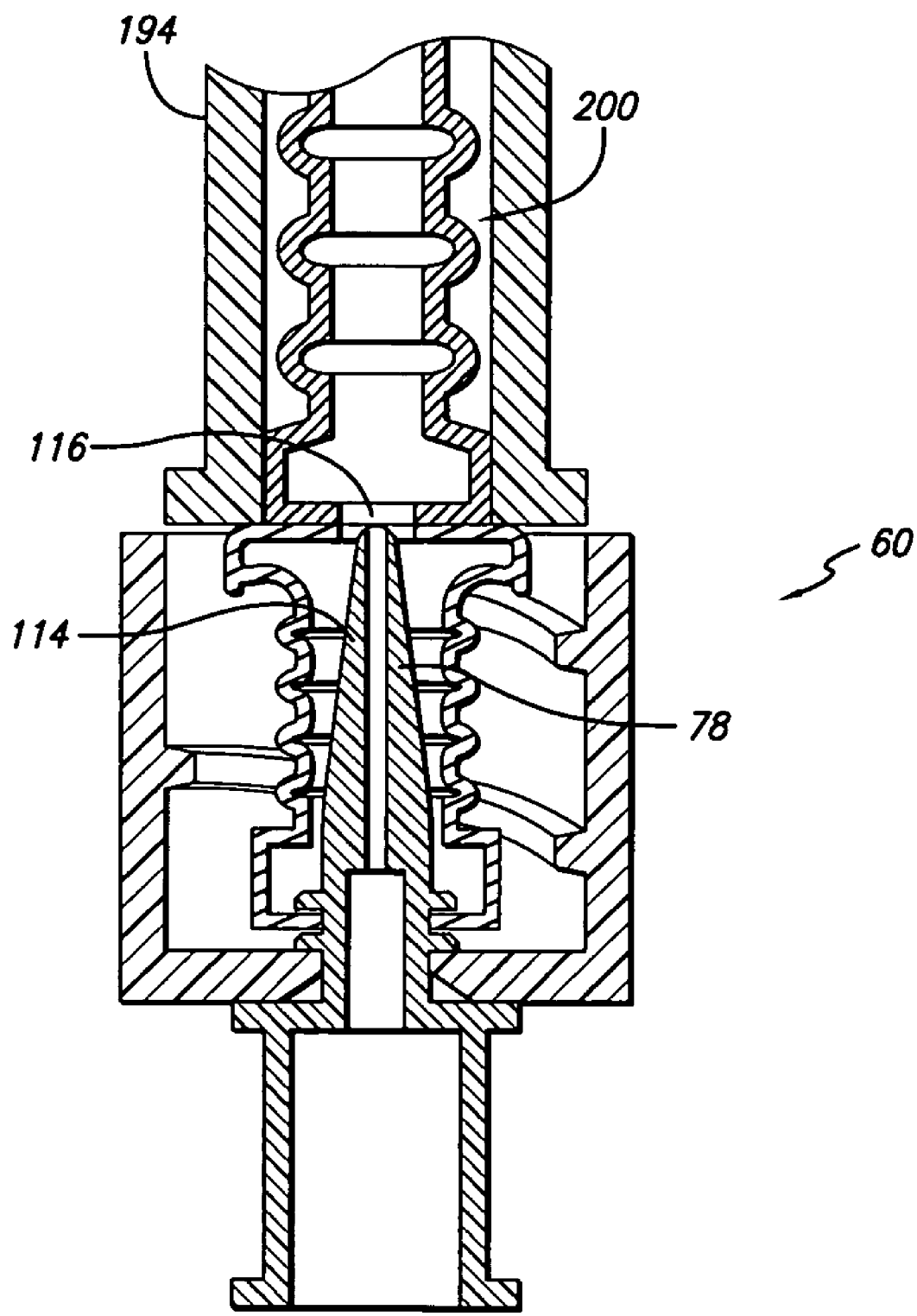
FIG. 11b is a front cross-sectional view similar to FIG. 11a except that the female Luer connector includes the internal piston, shown in FIG. 10b.

FIG. 11*b* shows a similar arrangement as FIG. 11*a* wherein the distal tip 114 of the post 78 has cleared the boot distal flange 152 and may now engage the piston 200 of the female connector 194. As the female Luer device is threadably advanced farther onto the self-sealing male Luer device 60, the post tip 114 will be able to press the female piston into the tube of the female connector, or may pierce the piston of the female device to establish fluid flow. Although not shown here, some self-sealing female Luer devices known in the art include a proximally-projecting post or spike that cooperates to open the female piston when the piston is compressed by engagement with a male connector. As such, the post tip 114 may also be configured, as discussed above, with a lumen 116 so as to engage the spike to center the connectors relative to one another and insure a direct flow path therebetween. In one case, the post 78 of the male connector shown here may have a reduced outer diameter so as to fit within the spike in the female Luer connector to establish fluid flow.

Figure 13A:
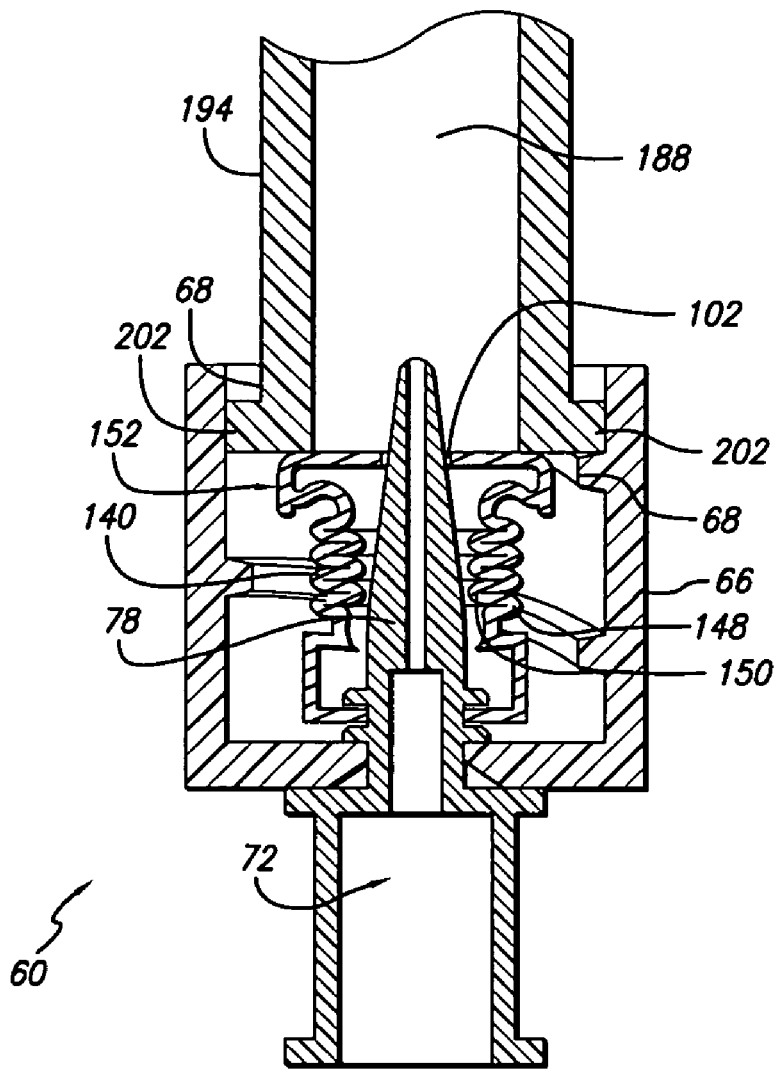
FIG. 13a is a front cross-sectional view of the male connector engaged with the female Luer connector as shown in FIGS. 10a and 11a with the female Luer connector secured on the male Luer device so as to be in contact with and fully compressing the boot for full fluid flow between the two connectors.

Referring now to FIG. 13*a*, there is shown the female Luer device 194 now fully threadably advanced onto the self-sealing male connector 60 within the thread hub 66. The engagement of the external thread portions 202 on the female Luer device with the internal threads 68 of the thread hub 66 is achieved by rotating the male hub 66 counter-clockwise, as viewed from its distal end, as the female Luer device is advanced proximally. After only approximately a one-half turn of the hub, the female Luer device will be securely engaged on the male Luer device as shown. In this position, the female Luer device will have been pulled proximately only about one-third of the way into the hub, but a sufficient distance to compress the spring 140 of the boot and cause the distal tip 114 of the post 78 to protrude through the slit 102 of the boot and into the flow passage 188 of the female connector 180.

Figure 14:
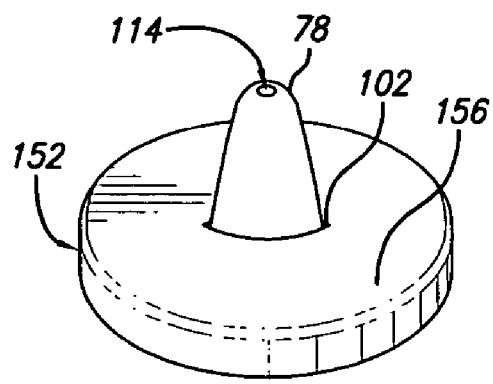
FIG. 14 is a partial top perspective view of the post of the male connector protruding through the slit of the boot in the configuration of FIGS. 13a and 13b.

FIG. 14 shows the protrusion of the distal tip 114 through the boot distal closure wall 156 of FIG. 13*a* in a top perspective view. It will be noted that the distal flange 152 of the boot fits snugly about the post 78 as it protrudes through the boot distal closure wall and substantially conforms to the circumference of the post.

Referring again to FIG. 13*a*, the effective axial compression of the spring section 140 of the boot 78 is achieved by the flexing of both the ribs 148 and the linear sections 150 between the ribs to create a stacked series of undulations. It will be appreciated that even as the boot is compressed, the configuration of the distal boot flange 152 enables the distal flange, and specifically its distal closure wall 156, to remain substantially planar and perpendicular to the boot's longitudinal axis 92 further enabling the boot to be compressed substantially axially and uniformly while a flat sealing surface continues to be presented to the female connector. In this way, as the female connector is pressed against the boot distal closure wall and is drawn farther into the thread hub 66, the rim 184 of the female connector forms a seal with the closure wall 156 during complete connection. Thus, flow through the male 60 and female 180 connectors will be confined to the post lumen 116 and the female connector flow passage 188.

Figure 13B:
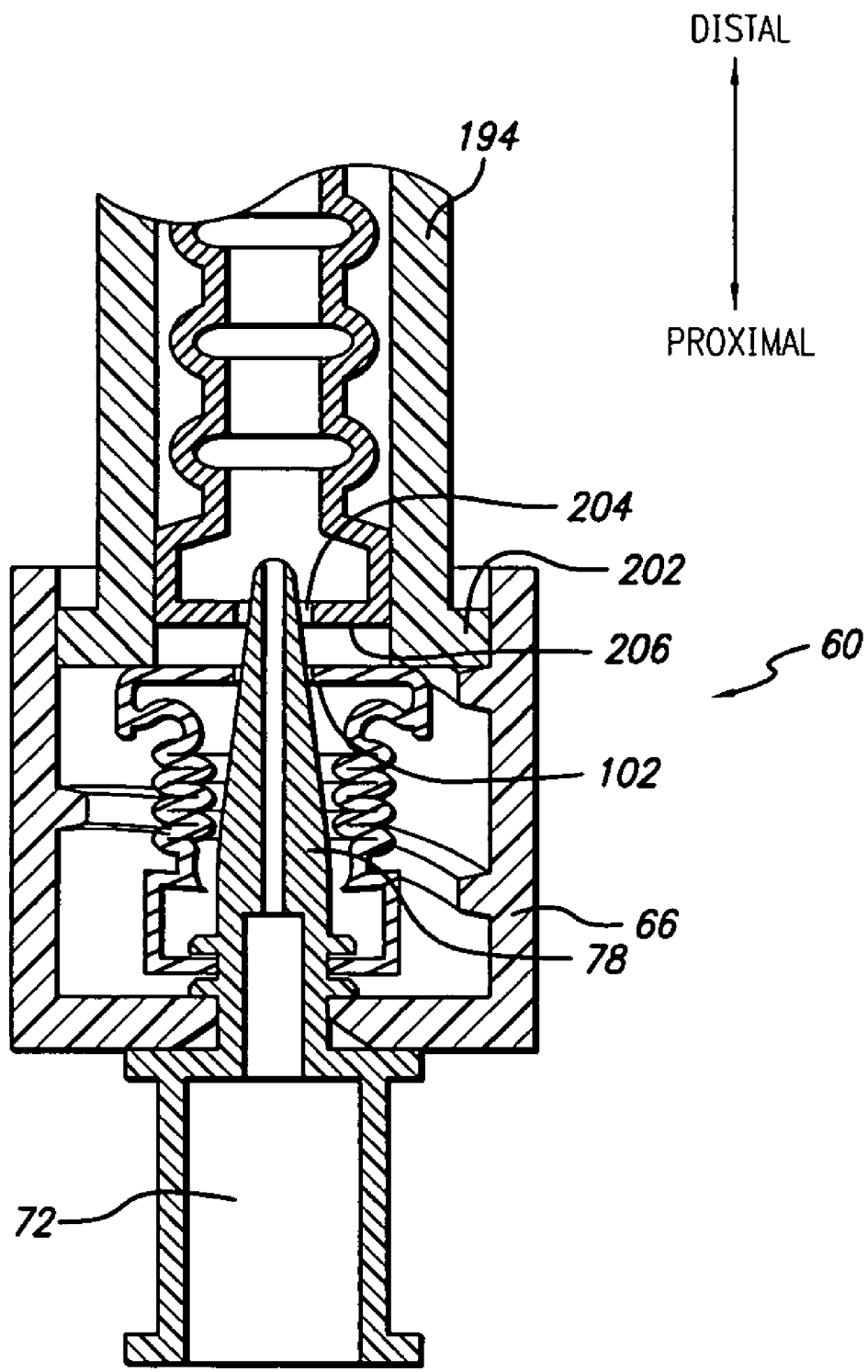
FIG. 13b is a front cross-sectional view of the male connector engaged with the female Luer connector as shown in FIGS. 10b and 11b with the female Luer connector secured on the male Luer device so as to be in contact with and fully compressing the boot for full fluid flow between the two connectors.

Turning now to FIG. 13*b* wherein the female Luer connector 194 includes an internal piston 200, it will be noted that the engagement of the female Luer connector's external thread portions 202 with the internal threads 68 of the male thread hub 66 has compressed the boot 64 causing a portion of the post tip 114 to protrude through the boot's slit 102. The distal post tip has also now protruded into the opening 204 in the piston's proximally-facing surface 206. A fluid communication path is thus established between the male and female Luer connectors 60 and 194.

Once the desired fluid exchange through the interconnected self-sealing male Luer device 60 and the female Luer device 194 is completed, the male Luer device may be disconnected by simply rotating the hub 66 to disengage the thread elements 202 of the female connector, allowing the female Luer connector to move in the distal direction away from the male connector. Simultaneously with the female connector's retraction away from the male connector, the spring section 140 of the boot 64 expands toward its at-rest, uncompressed condition allowing the distal boot flange to move down the taper of the post thereby maintaining contact between the boot's distal closure wall 156 and the female Luer device's proximally-facing rim 184, preventing any fluid escape. At the same time, as the boot expands and its length increases, the boot moves back toward a covering relationship about the post tip 66, with the post tip's nose 68 just visible within the almost closed boot slit 106, as shown in FIG. 12. Thus, the boot again completely encloses the post tip 114 and the slit 102 in the boot's distal closure wall 156 returns to its closed position, as shown in FIG. 2, thereby sealing off the male Luer connector 60 and trapping all remaining fluid within the post's internal lumen 116. Similarly, as the female Luer connector 194 disengages the male connector 60, the piston 200 of the female connector reseals itself as the post 78 is withdrawn from the female fluid passage 198. In this way, disconnection of the male Luer device 60 from the female Luer device 194 simultaneously causes the boot to reseal the distal end of the male Luer connector, making the connection and disconnection of a syringe adapted with the self-sealing male Luer device of the present invention convenient, safe, and effective.

It will be further appreciated by those skilled in the art that when the male Luer device 60 is in its at-rest configuration before and after use, as best shown in FIG. 2, the distal boot flange 152 (FIG. 6) is easily accessible. Thus, the distal closure wall 156 of the boot flange may be easily wiped, sprayed with a disinfectant, or otherwise cleaned so as to eliminate any possible contaminants. Alternatively, the entire male Luer device may be made of sterilizable plastic materials known in the art to be suited for safe and effective use in ethylene oxide, gamma radiation, electron beam radiation, autoclaving, or other such sterilization procedures.

Figure 15:
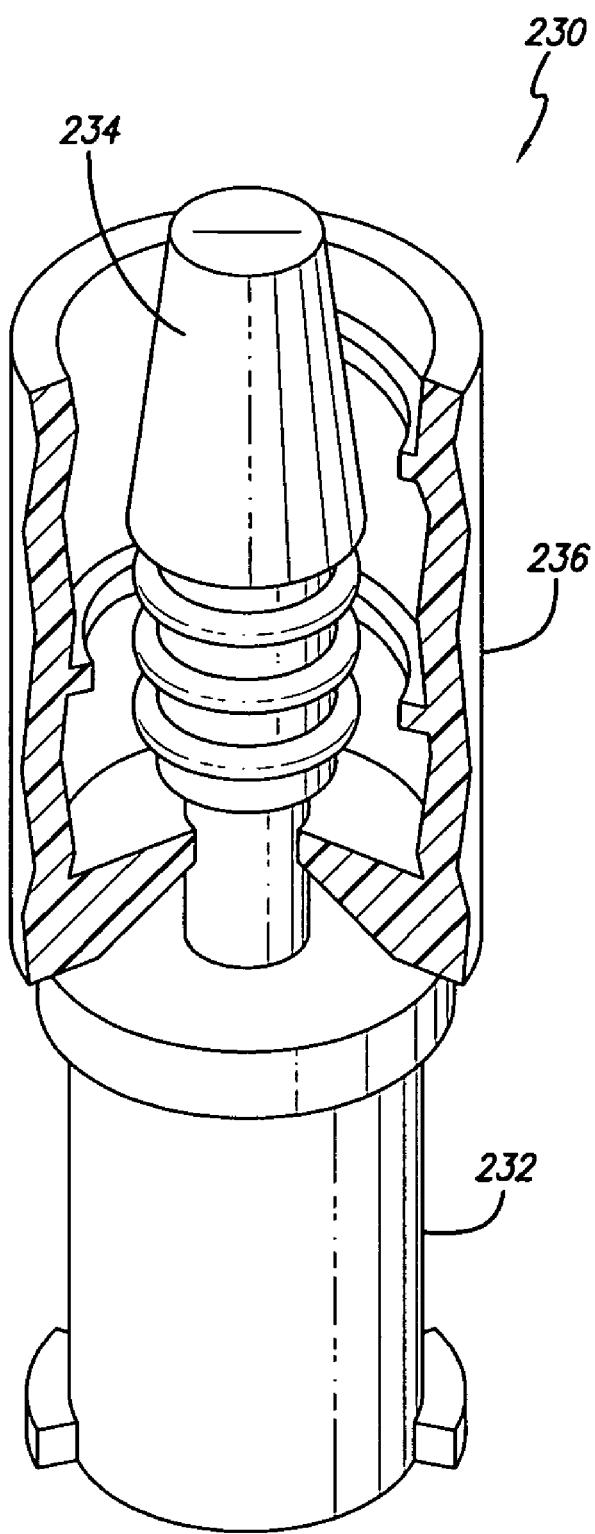
FIG. 15 is a top perspective view of an alternative embodiment of a self-sealing male connector in accordance with aspects of the invention having a body, a resilient boot, and a male thread hub, partially cut away so that the internal configuration can be more clearly seen.

Turning now to FIG. 15, there is shown another embodiment of a self-sealing male Luer device 230 having a body 232, a resilient boot 234, and a male Luer hub 236. In this embodiment, the body 232 and the hub 236 are substantially the same as the body 62 and the hub 66 shown in the first exemplary embodiment of FIG. 2, while the configuration of the boot 234 of FIG. 15 has been modified from that of the boot 64 of FIG. 2.

Figure 16:
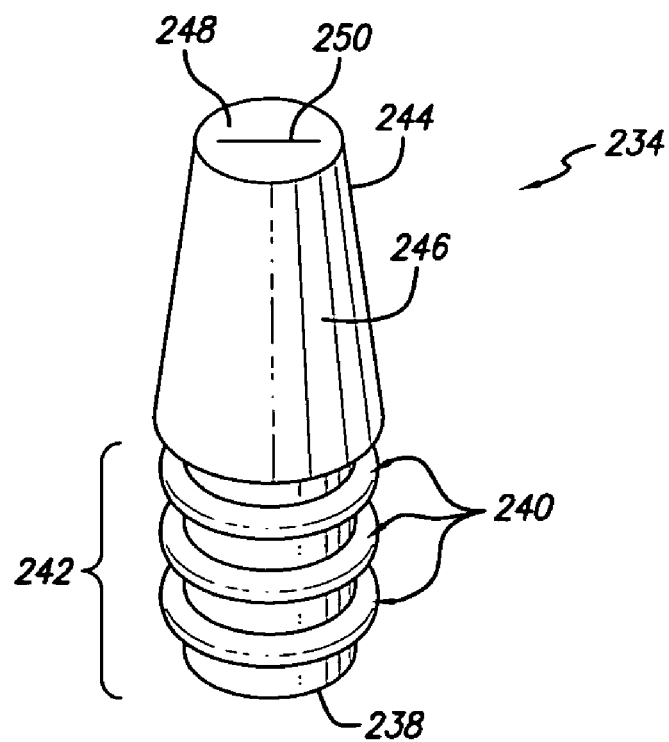
FIG. 16 is a top perspective view of the resilient boot shown in FIG. 15, the boot including a proximal mounting lip, a tapered section, and a spring section.

With reference to FIG. 16, there is seen a top perspective view of the boot 234 employed in the alternative male Luer connector 230 shown in FIG. 15. The boot has a proximal end 238 configured in the exemplary alternative embodiment with three spaced-apart circumferential ribs 240 defining a spring section 242. The distal end 244 of the boot is configured in this embodiment to have a circular periphery that has tapered down from a larger circular periphery at the boot's proximal end. This tapered region is designated by numeral 246 in FIG. 16. The spring section 242 is integral with the proximal end of the boot in this embodiment. The distal end 244 terminates in a distal closure surface 248 that is substantially planar in this embodiment. The distal closure surface is formed with a diametrical slit 250 configured much like the slit 102 shown in FIG. 2, for selectively sealing off the distal tip of the post or allowing a portion of the post tip to protrude therethrough during use.

Figure 17:
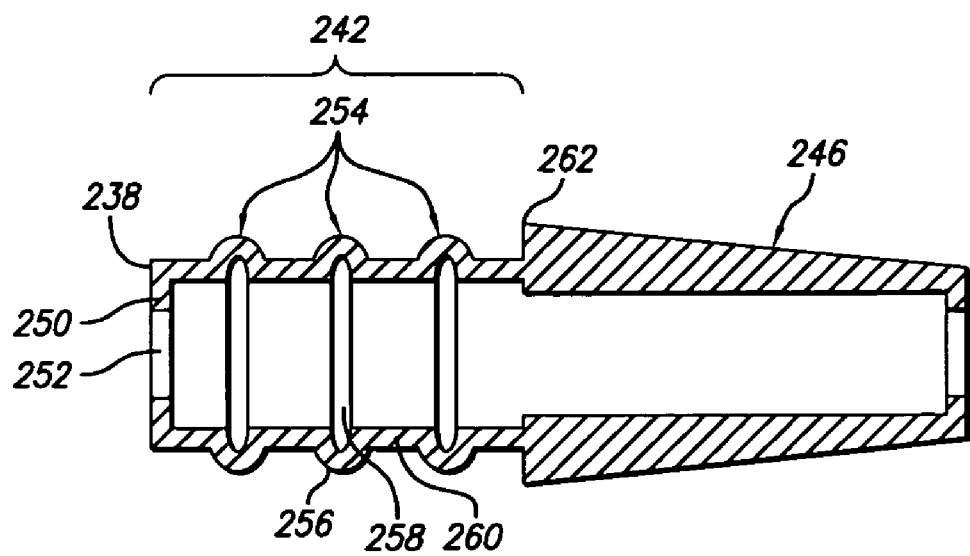
FIG. 17 is a front cross-sectional view of the boot of FIG. 16.

Referring now to FIG. 17, a cross-sectional view of the boot 234 shown in FIG. 16 is provided. The proximal end 238 of the boot is formed with a radially inwardly projecting boot lip 250 defining an annular boot opening 252, as in the embodiment of FIG. 2. The proximal end of the boot transitions to the spring section 242 which is the similar to the spring section of FIG. 2 except that the current spring section is shown with three ribs, rather than four. The circumferential ribs have an arcuate section 256 and a corresponding interior groove 258, and are interconnected by linear sections 260 as in the spring section shown in FIG. 7. The distal end of the spring section then transitions to the proximal end 262 of the tapered boot section 246.

Turning to FIG. 118a, assembly of the sealed male connector 230 can be seen. As in the embodiment shown in FIG. 2, the male thread hub 236 is first slid over the post and snapped onto the body 232 in a first mounting groove 266. Next, the boot 234 is engaged with a second mounting groove 268 in the body to firmly mount the boot in covering relationship about the body's post 264. The male connector is then completely assembled.

Figure 18A:
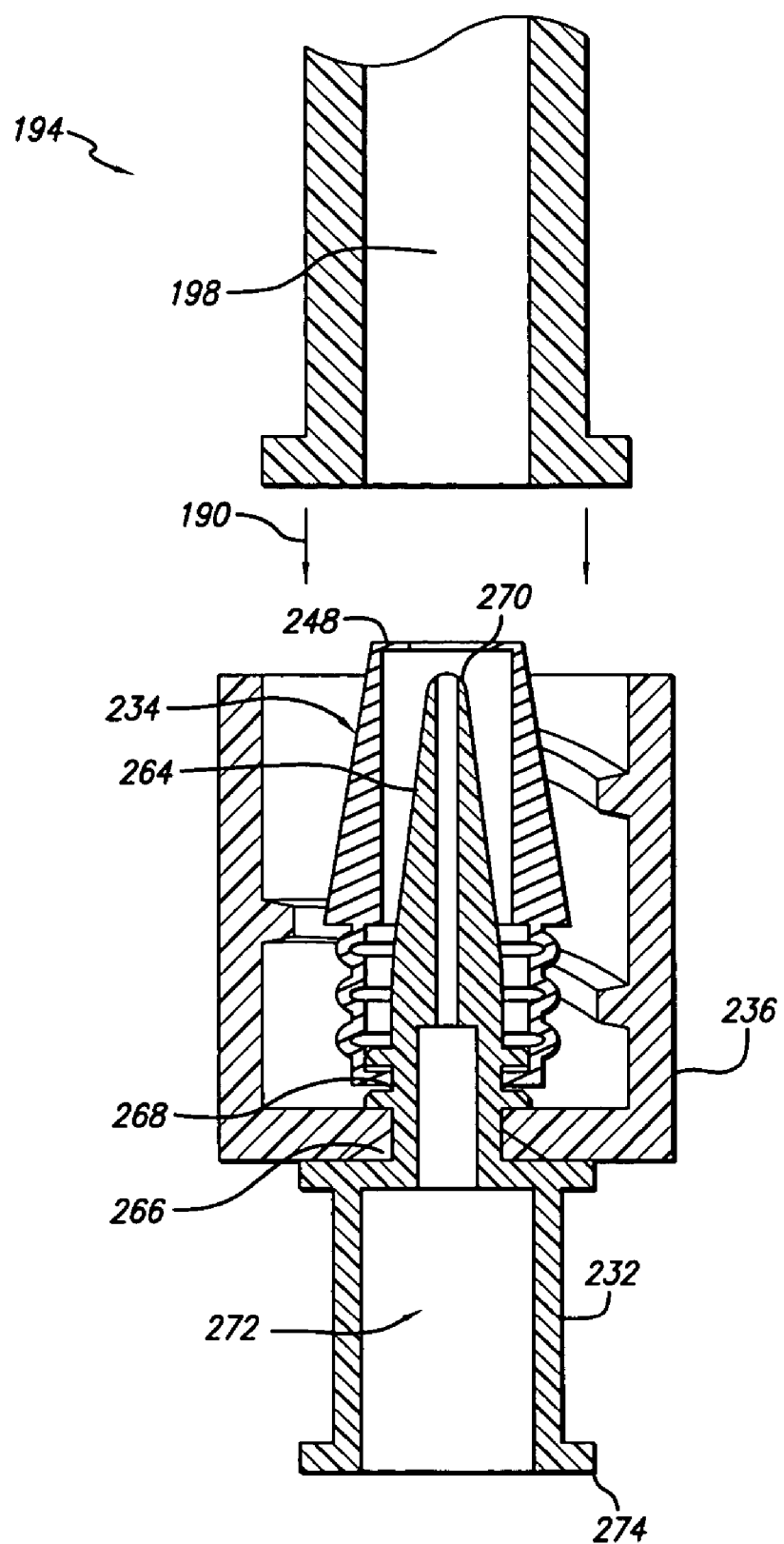
FIG. 18a is a front cross-sectional view of the self-sealing male connector shown in FIG. 15 and further showing a cross-sectional view of an adjacent conventional female Luer connector in position to be engaged with the male connector.
Figure 18B:
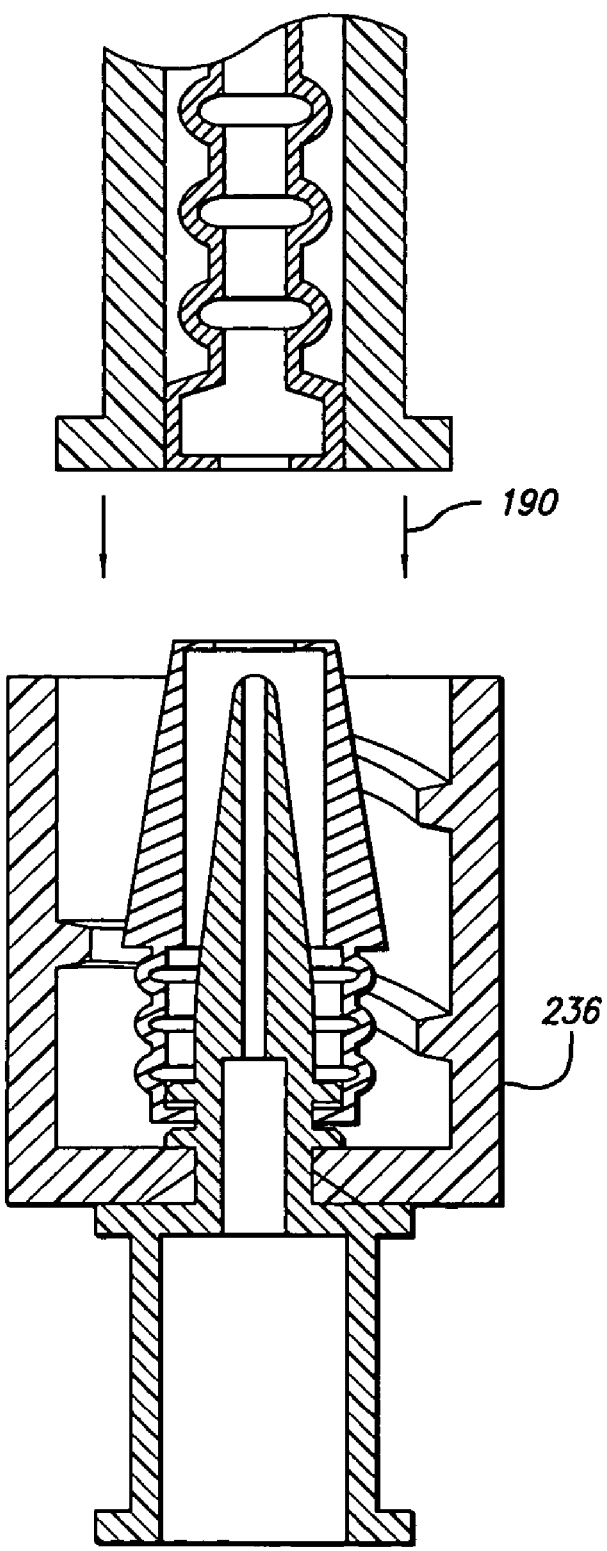
FIG. 18b is a front cross-sectional view of the self-sealing male connector shown in FIG. 15 and further showing a partial cross-sectional view of an adjacent self-sealing female Luer connector in position to be connected to the male connector, the female connector in this case having an internal sealing piston.
Figure 19A:
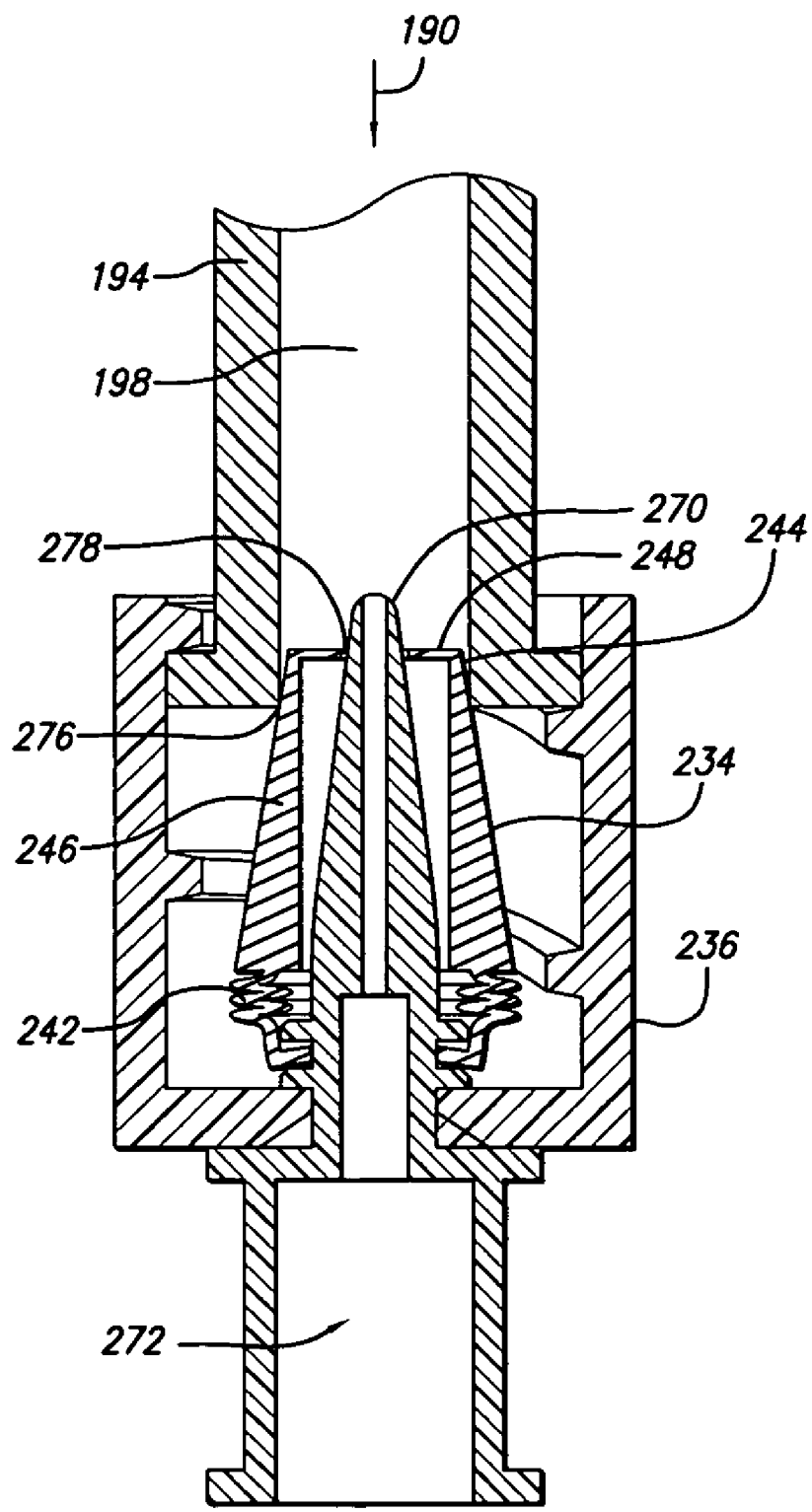
FIG. 19a is a front cross-sectional view of the male connector and female connector of FIG. 18a with the female Luer connector engaged with the male connector so as to be in contact with and compressing the boot to allow fluid flow.
Figure 19B:
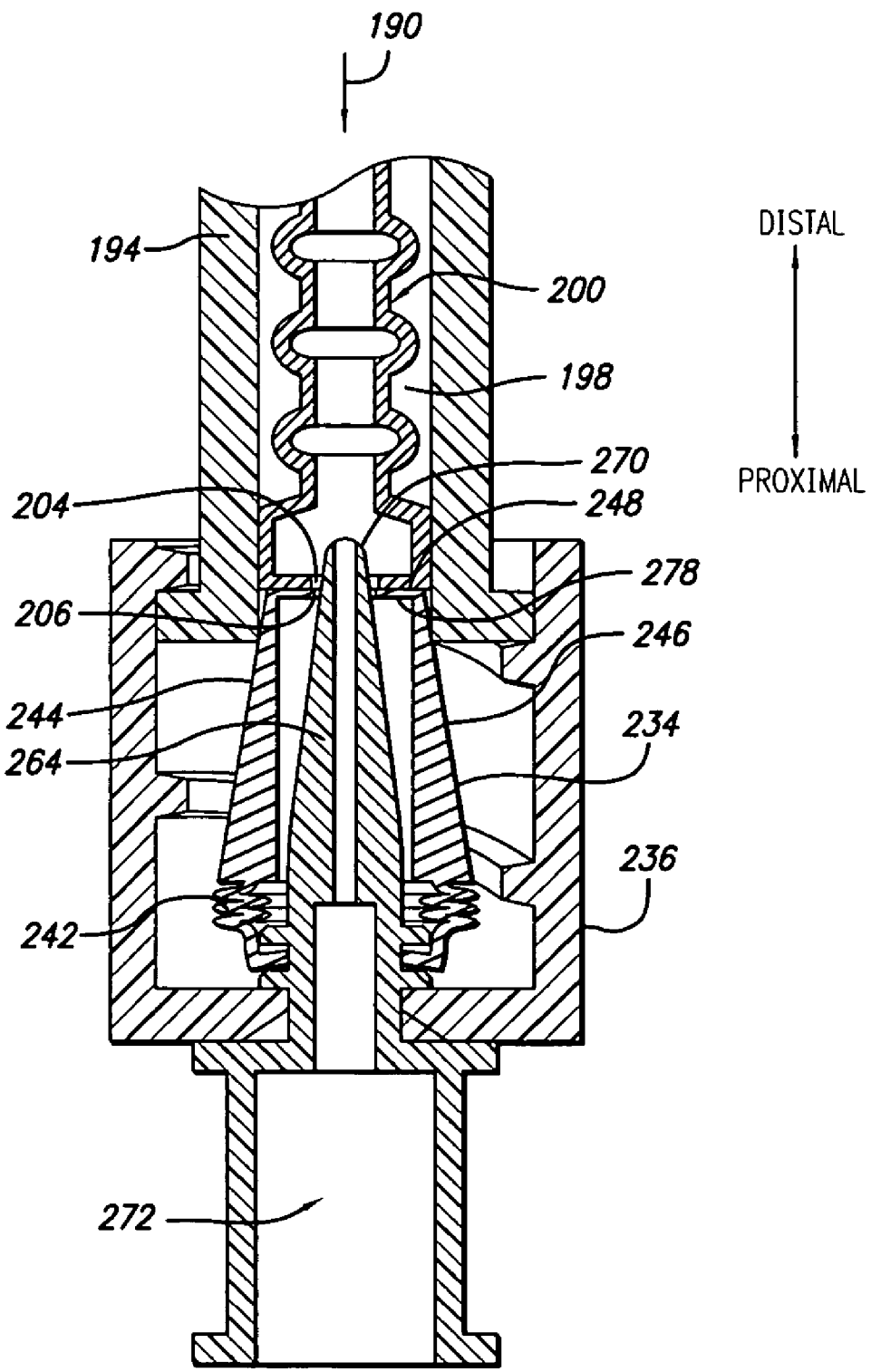
FIG. 19b is a front cross-sectional view of the male connector and female connector of FIG. 18b with the female Luer connector engaged with the male connector so as to be in contact with and compressing the boot to allow fluid flow and showing interaction of the male connector post with the female piston.

Beginning with reference to FIG. 18a, engagement of the alternative embodiment of the sealed male connector 230 with a female connector 194 is shown. In FIGS. 18a and 19a, engagement of the male connector with a female connector having no piston is shown and in FIGS. 18b and 19b, engagement of the male connector with a female connector having an internal piston valve is shown. The use of the thread hub 236 and post 264 is essentially the same as the first embodiment as shown in FIGS. 10a through 13b.

The boot 234 is configured such that when mounted on the body 232 in its at-rest, uncompressed condition, the boot fully encloses the distal tip 270 of the post and prevents fluids within the body's internal lumen 272 and a connected syringe from escaping. It will be noted from FIG. 18a that the diameter of the distal closure surface 248 of the boot 234 is smaller than the inner diameter of the female connector's fluid flow passage 198.

Referring now to FIG. 19a, as the female Luer connector 194 is advanced in the proximal direction and the threads of the connectors engage each other, the distal end 244 of the boot 234 enters the female Luer device's fluid flow passage 198. Because the outside diameter of the distal end of the tapered boot tip 234 is smaller than the inside diameter of the through-hole, the tip is able to enter and center itself within the through-hole. In one embodiment, to facilitate such engagement between the male and female connectors, the boot's tapered section is substantially equivalent to the ANSI/AAMI/ISO male Luer connector dimensions. However, in the embodiment of FIG. 19a, the tapered section of the boot reaches an outer diameter that is larger than the opening of the female connector's fluid flow passage and the rim contacts that part of the boot and begins to compress the boot. Thus, the post distal tip protrudes through the slit 278 and into the female Luer connector's fluid flow passage.

Therefore, as shown in FIG. 19a, when the tapered surface 246 of the boot 234 seats within the flow passage 198 of the female connector 194 and the boot distal end 244 is unable to protrude any farther into the passage, continued proximal advancement of the female Luer connector onto the male connector will result in compression of the resilient boot's spring section 242, as shown. In the embodiment shown, the location at which the diameter of the tapered boot surface is substantially equivalent to that of the flow passage of the female connector causing the tapered surface to seat therein, is closer to the boot's distal tip so that approximately one-third of the boot tip's overall length will protrude into the female Luer device before its tapered surface engages the through-hole. Further advancement of the female Luer connector within the male thread hub 236 compresses the spring and causes the distal tip 270 of the post 264 to protrude through the slit 278 of the boot tip. As in the embodiment shown in FIG. 14, the slit fits snugly about the protruding post. Moreover, a fluid-tight seal is formed between the boot and the fluid passage of the female connector when the tapered boot tip seats within the female connector's passage thereby preventing unwanted fluid escape.

Similar to FIGS. 10b, 11b, 13b, 18a, and 19a, the same male connector 230 is mounted to a female connector 194 having an internal piston seal 200. It will be noted from FIGS. 19a and 19b that as the female Luer device is advanced proximally in the direction of arrows 190, the boot's distally-facing surface 248 is brought into contact with the female piston's proximally-facing surface 206. As the female Luer device 194 is advanced further toward the male connector 230 after the proximally- and distally-facing surfaces of the respective piston 206 and boot 248 are brought into contact, the compression forces generated by any spring on the female connector's piston and the resilient boot spring 242 of the male connector will dictate which member is initially compressed. In either case, when the thread hub 236 pulls the female connector far enough into contact with the male connector 230, the distal tip 270 of the post 264 will partially protrude through the slit 278 in the male connector's boot 234 and through the adjacent slit 204 or other opening in the female connector's piston 200, whereby a fluid flow path between the male and female connectors is established.

It will be appreciated by those skilled in the art that the connection of the female connector 194 with the self-sealing male Luer connector 230 is substantially leak-proof, as the boot tip 244 is in contact with the female's flow passage 198 and with the protruding post tip 270. Likewise, during disconnection of the female connector, the spring section 242 of the boot will expand as the female Luer connector is withdrawn, maintaining contact between the opposing male boot and female piston surfaces 248 and 206 until the boot returns to its at-rest, uncompressed configuration shown in FIG. 18b, thereby fully enclosing the post tip before the distally-facing surface of the boot tip is disengaged from the piston's proximally-facing surface. Moreover, as with the embodiment of the boot 64 shown in FIG. 2, the distal closure surface 248 of the boot and a substantial portion of the boot's tapered surface 246 are easily accessible so that they may be cleaned for safe handling, storage, or subsequent use.

In both the boot embodiments 64 and 234 of FIGS. 7 and 17, respectively, it will be appreciated that the interior profile of the respective boots is larger than and substantially conforming to the exterior profile of the post 78 and 264, respectively. This may be seen in FIGS. 10a, 13a, 18a, and 19a. In this way, as the boots are compressed along the post during connection of the sealed male connector 60 and 230 to a female connector, the inside surface of the boot will not in any way bind on the post's outside surface. Rather, the size and shape of the boot's interior profile and the clearance provided between it and the post's exterior profile facilitate smooth movement of the respective boots in and out about the post during use. It will be appreciated that while the post and boot are described and shown as being substantially circular in cross-section, it will be appreciated by those skilled in the art that other cross-sectional configurations may be employed to achieve the desired result.

Figure 20:
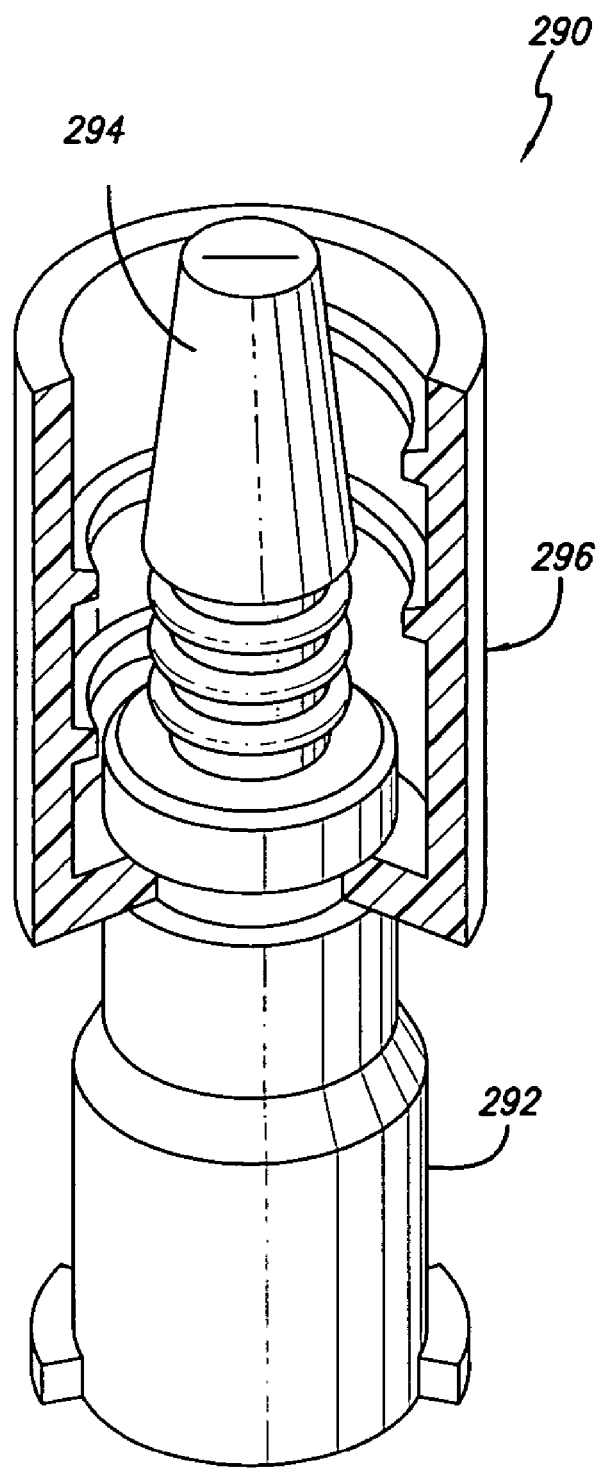
FIG. 20 is a top perspective view of a further alternative embodiment of the self-sealing male connector in accordance with aspects of the invention, the connector also having a central body, a resilient boot, and an annular threaded male hub partially cut away so that the arrangement of the connector can be seen more clearly.

Referring now to FIG. 20, there is seen a top perspective view of another alternative embodiment of a self-sealing male connector 290 in accordance with aspects of the present invention. This sealed male connector includes a body 292, a resilient boot 294, and a male thread hub 296. While this embodiment of the sealed male connector 290 is depicted as including a post and a boot that appear similar to those shown in FIG. 15, some differences exist. It will be appreciated that changes may be made to various parts of the connector shown.

Figure 21:
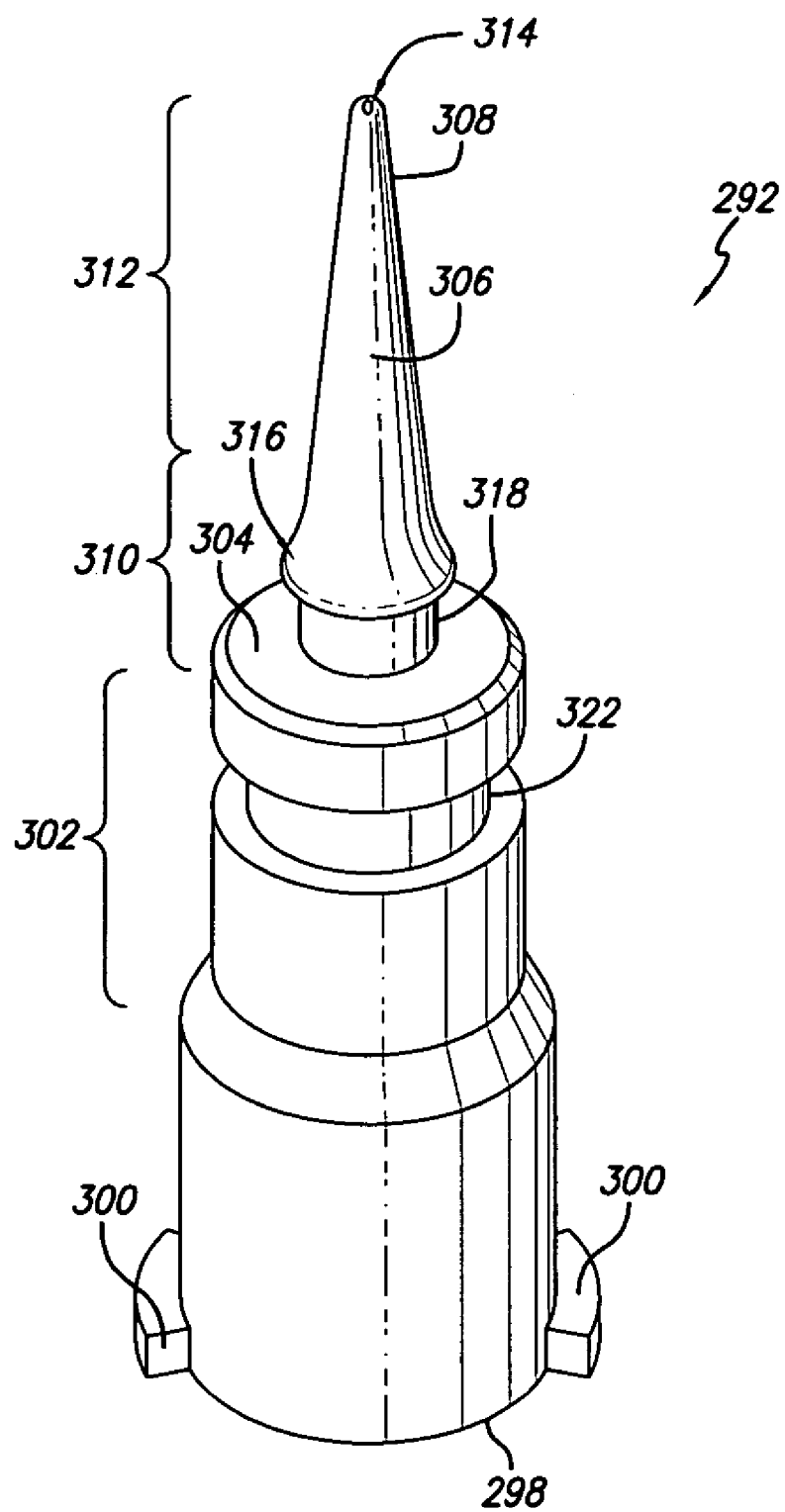
FIG. 21 is a top perspective view of the body of the male connector shown in FIG. 20, the body including a proximal female connector, an intermediate portion having a thread hub mounting groove, and a distal tapered post with a boot mounting flange.

In FIG. 21 there is shown a top perspective view of the body 292 of the embodiment of FIG. 20. The body has a proximal end 298 configured as a female Luer connector with external thread portions 300. The proximal end transitions in the distal direction to a stepped-down, smaller diameter interim body portion 302 terminating distally in a distally-facing shoulder 304. An elongate post 306 extends distally from the shoulder 304 and is substantially centered thereon. The post extends to the distal end 308 of the body. The post has a proximal base 310 that is of a generally constant diameter and a tapered portion 312 that is tapered along its length from a larger diameter at the post base to a smaller diameter post tip 314. A radial flange 316 is formed circumferentially about the base of the post distal to the shoulder 304. The flange 316 results in a second groove 318 disposed between the flange and the shoulder for retaining the boot. It should be noted, as in other embodiments, that the groove may be formed by molding the flange or by later removing material from the post, or in other ways.

Formed in the interim body section 302 is a first groove 322 for receiving the thread hub 296. Once snapped into place, in one embodiment, the longitudinal movement of the thread hub is restrained by the groove edges. While some longitudinal movement may be allowed, it is restricted. Likewise, in one embodiment, the hub may rotate about the body in the first groove to assist in mounting a female connector to the sealed male connector.

In the present embodiment, the post is more slender than previous posts. As such, the post may be able to protrude through and seat within a variety of female Luer connectors now known or later used in the art. To facilitate the design and manufacture of the narrow post configuration of this embodiment, the body may be formed from a relatively high strength metal or polymer through a metal injection molding ("MIM") process.

Figure 22:
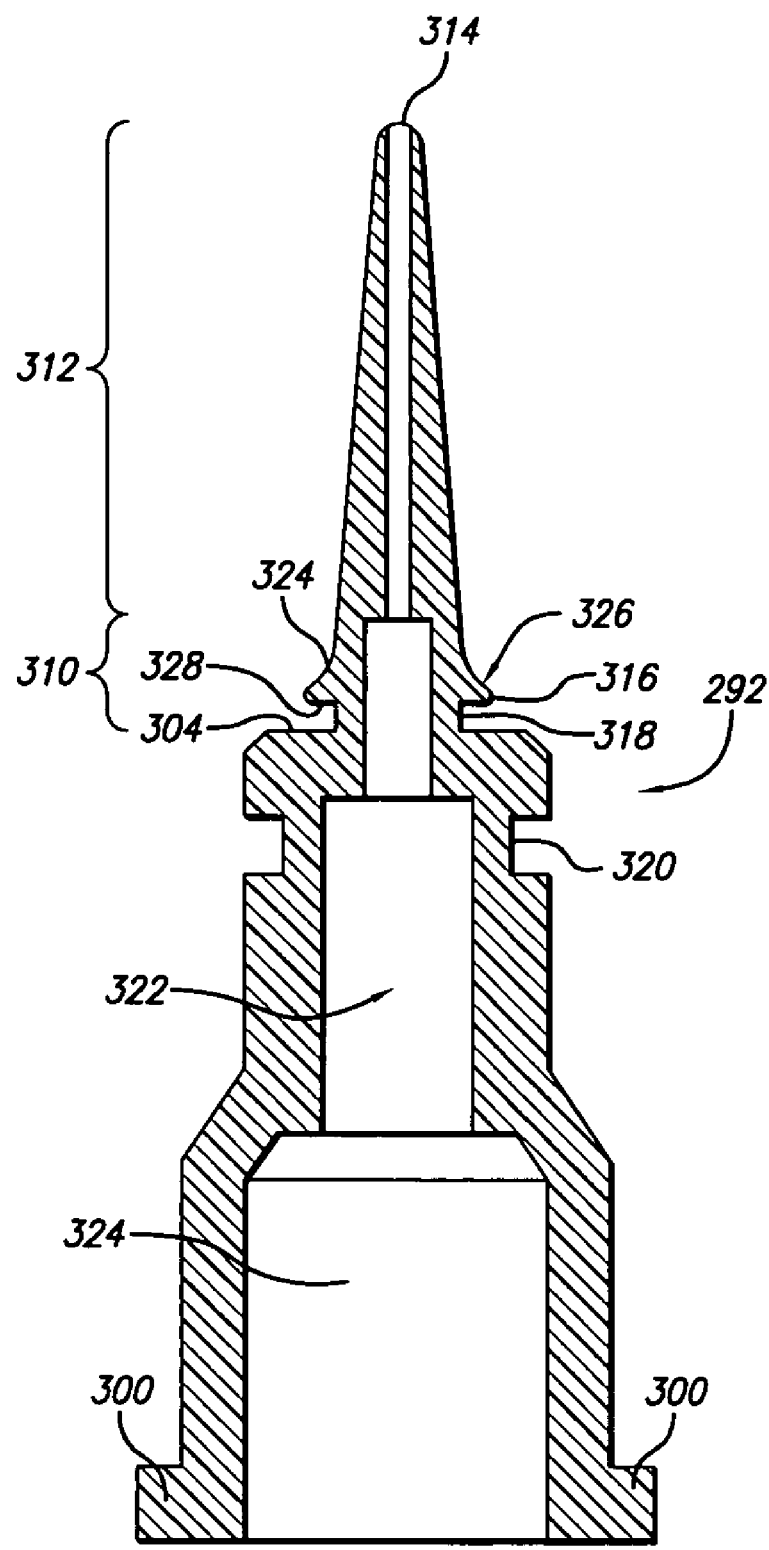
FIG. 22 is a front cross-sectional view of the body shown in FIG. 21.

Turning now to FIG. 22, a side, cross-sectional view is seen of the body 292 shown in the perspective view of FIG. 21. The internal lumen 322 comprises stepped diameter sections. The proximal lumen section 324 is shaped as a female Luer connector having a standard tapered wall. The distal portion of the proximal lumen section is shown as terminating in an angled or filleted edge. It will be appreciated that various stepped lumen configurations may be provided within the body so as to achieve the desired wall thickness and the necessary fluid flow path between the body's proximal and distal ends.

As also shown in FIG. 22, the post flange 316 is formed having a leading or distal flange edge 326 that is chamfered to facilitate the passage of the boot mounting surfaces over the flange in the proximal direction in order to seat within the second groove 318. The proximal flange edge 328 has a substantially square profile providing a well-defined edge for the retention of the boot mounting surfaces. Similarly, the shoulder 304 of the body is chamfered to facilitate the proximal installation of the thread hub over the body to snap into the first groove 320. The first groove is formed with a square profile so as to optimally retain the thread hub on the body and limit its axial movement while allowing it to rotate within the groove.

Figure 23:
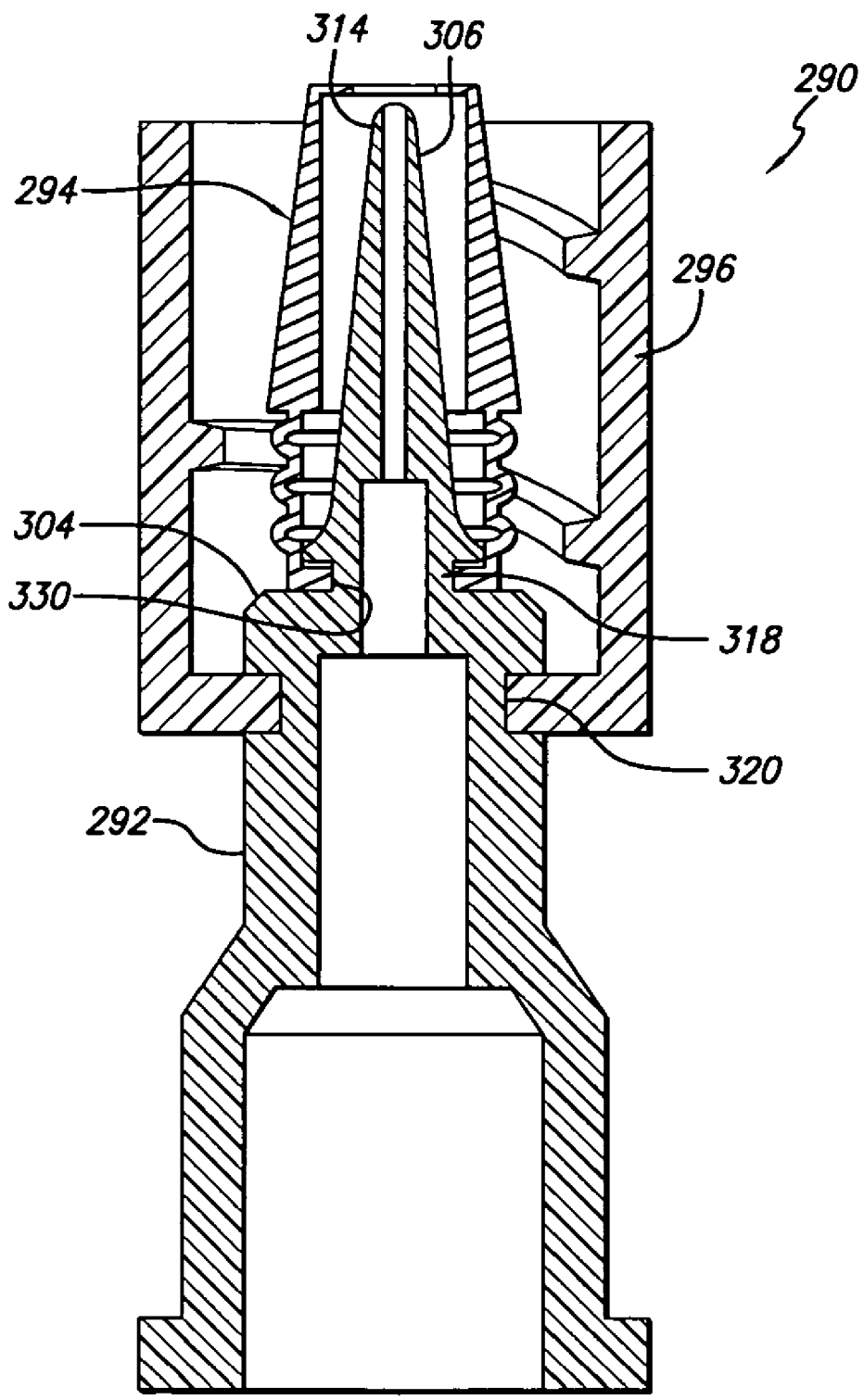
FIG. 23 is a front cross-sectional view of the male connector device shown in FIG. 20.

With reference now to FIG. 23, the self-sealing male connector 290 is assembled by sliding the thread hub 296 over the post 306 and over the shoulder 304 and snapping the hub into the first groove 320 in the body. Secondly, the boot 294 is mounted on the post by engaging the proximal boot opening 330 within the second groove 318, formed in the post. The boot will then completely enclose the post tip 314. The male connector 290 of FIG. 23 is engaged with a female connector in the same manner as is shown and described for other embodiments previously.

Therefore, the self-sealing male Luer device of the present invention is well suited for connection to a syringe or other dispenser used to transfer nuclear medicines, chemotherapy medicines, or the like to a patient without compromising the patient's or care giver's safety. Because of the small number of parts and their easy assembly, cost is lowered while performance is improved. It should be noted from FIGS. 2, 15, and 20, that nothing is disposed between the hub, or other connecting device, and the boot. This results in a smaller number of parts and should lower manufacturing costs. It should also be noted that although the embodiments showed a linear connector, that is where the two openings of the connector are aligned, the orientation of the openings could be otherwise. For example, the openings could be at right angles to each other, or be oriented otherwise.

While particular forms and uses of embodiments of the invention have been illustrated and described, it will also be apparent to those skilled in the art that various modifications can be made without departing from the scope of the invention. Accordingly, it is not intended that the invention be limited except by the appended claims.

What is claimed is:

1. A self-sealing male connector for connection with a female connector having an opening for fluid flow in a tubular body, the tubular body having a proximal rim with a first engagement device disposed adjacent the opening, the male connector comprising:
    a body comprising:
        a proximal end having a proximal opening for fluid flow;
        an elongated post extending in a distal direction having a distal tip forming the distal end of the body and having a distal opening at the distal tip for fluid flow, the post having an outside surface;
        a fluid flow passage extending through the body from the proximal opening to the distal opening, the post having an outer diameter at the distal tip that is small enough to fit within the fluid flow opening of the female connector;
    a resilient boot mounted to the body and extending in covering relationship over the outside surface of the post to seal the distal opening of the post, the boot having a longitudinal axis and a distal end flared radially outwardly to form an enlarged, hollow distal flange, the flange having a generally planar shape and comprising a distal facing closure wall having an opening and providing a sealing surface for the female connector rim, the flange further comprising a proximal surface connected with an annular side wall to the closure wall adapted to provide stability to the closure wall and to maintain the generally planar shape of the flange when the resilient boot is compressed;
    wherein the configuration of the distal flange enables the distal flange and the closure wall to remain substantially planar and perpendicular to the boot's longitudinal axis further enabling the boot to be compressed substantially axially and uniformly while a flat sealing surface continues to be presented to the female connector; and
    a second engagement device mounted to the body, the second engagement device adapted to interact with the first engagement device of the female connector to secure the female and male connectors together in an engaged configuration, wherein the second engagement device comprises a thread hub mounted to the body, the thread hub having internal threads for engaging threads on the exterior of the female connector.

2. The self-sealing male connector of claim 1 wherein:
    the post tip terminates in a substantially rounded nose so as to have a nose apex;
    the internal lumen terminates proximally of the nose apex; and
    one or more radial cross-holes are formed in the post tip so as to communicate with the internal lumen with openings of the cross holes being oriented in a radial direction.

3. The self-sealing male connector of claim 1 wherein a cross-notch is formed through the post tip substantially at the nose apex so as to form opposing distally-projecting teeth at the post tip to facilitate opening a slit in the distal end of the boot and the passage of the post tip therethrough.

4. A self-sealing male connector for connection with a female connector having an opening for fluid flow in a tubular body, the tubular body having a proximal rim with a first engagement device disposed adjacent the opening, the male connector comprising:
    a body comprising:
        a proximal end having a proximal opening for fluid flow;
        an elongated post extending in a distal direction having a distal tip forming the distal end of the body and having a distal opening at the distal tip for fluid flow, the post having an outside surface;
        a fluid flow passage extending through the body from the proximal opening to the distal opening, the post having an outer diameter at the distal tip that is small enough to fit within the fluid flow opening of the female connector;
    a resilient boot mounted to the body and extending in covering relationship over the outside surface of the post to seal the distal opening of the post, the boot having a longitudinal axis and a distal end flared radially outwardly to form an enlarged, hollow distal flange, the flange having a generally planar shape and comprising a distal facing closure wall having an opening and providing a sealing surface for the female connector rim, the flange further comprising a proximal surface connected with an annular side wall to the closure wall adapted to provide stability to the closure wall and to maintain the generally planar shape of the flange when the resilient boot is compressed;
    wherein the configuration of the distal flange enables the distal flange and the closure wall to remain substantially planar and perpendicular to the boot's longitudinal axis further enabling the boot to be compressed substantially axially and uniformly while a flat sealing surface continues to be presented to the female connector; and
    a second engagement device mounted to the body, the second engagement device adapted to interact with the first engagement device of the female connector to secure the female and male connectors together in an engaged configuration, the second engagement device comprising a thread hub mounted to the body, the thread hub having the internal threads for engaging threads on the exterior of the female connector;

wherein the distal flange having has an outside dimension greater than the inside diameter of the female connector fluid flow opening, the boot being further configured such that engagement of the first and second engagement devices brings the boot's closure wall into contact with the female connector's rim and positions the opening of the closure wall substantially adjacent the female connector's opening so that as the female and male connectors are brought closer into an engagement relationship, the boot is compressed and the post tip protrudes through the opening of the closure wall and at least partially into the female connector's opening.

5. A self-sealing male connector for connection with a female connector having an opening for fluid flow in a tubular body, the tubular body having a proximal rim with a first engagement device disposed adjacent the opening, the male connector comprising:

a body comprising:
  a proximal end having a proximal opening for fluid flow;
  an elongated post extending in a distal direction having a distal tip forming the distal end of the body and having a distal opening at the distal tip for fluid flow, the post having an outside surface;
  a fluid flow passage extending through the body from the proximal opening to the distal opening, the post having an outer diameter at the distal tip that is small enough to fit within the fluid flow opening of the female connector;
  a resilient boot mounted to the body and extending in covering relationship over the outside surface of the post to seal the distal opening of the post, the boot having a longitudinal axis and a distal end flared radially outwardly to form an enlarged, hollow distal flange, the flange having a generally planar shape and comprising a distal facing closure wall having an opening and providing a sealing surface for the female connector rim, the flange further comprising a proximal surface connected with an annular side wall to the closure wall adapted to provide stability to the closure wall and to maintain the generally planar shape of the flange when the resilient boot is compressed;
  wherein the configuration of the distal flange enables the distal flange and the closure wall to remain substantially planar and perpendicular to the boot's longitudinal axis further enabling the boot to be compressed substantially axially and uniformly while a flat sealing surface continues to be presented to the female connector; and
  a second engagement device mounted to the body, the second engagement device adapted to interact with the first engagement device of the female connector to secure the female and male connectors together in an engaged configuration, the second engagement device comprising a thread hub mounted into a first groove of the body, the thread hub having internal threads for engaging threads on the exterior of the female connector.

6. The self-sealing male connector of claim 5 wherein the body has a second groove into which is mounted the boot.

7. The self-sealing male connector of claim 6 wherein the thread hub is rotatably mounted to the first groove so it can rotate independently of the body; whereby the body and female connector may remain rotationally stationary while being engaged together while the thread hub is rotated to fasten the female and male together.

8. The self-sealing male connector of claim 7 wherein the hub is formed at a proximal end with a radially inwardly projecting annular hub flange defining an annular first hub opening, the hub flange being configured for receipt within the first groove so as to rotationally mount the hub onto the body while axially trapping the hub flange within the first groove so as to limit the hub's longitudinal movement.

9. The self-sealing male connector of claim 6 wherein the first and second grooves are formed on a proximal base of the post.

10. A self-sealing male connector for connection with a female connector having an opening for fluid flow in a tubular body, the tubular body having a proximal rim with a first engagement device disposed adjacent the opening, the male connector comprising:

a body comprising:
  a proximal end having a proximal opening for fluid flow;
  an elongated post extending in a distal direction having a distal tip forming the distal end of the body and having a distal opening at the distal tip for fluid flow, the post having an outside surface and having a mounting groove;
  a fluid flow passage extending through the body from the proximal opening to the distal opening, the post having an outer diameter at the distal tip that is small enough to fit within the fluid flow opening of the female connector;
  a resilient boot mounted to the body and extending in covering relationship over the outside surface of the post to seal the distal opening of the post, the boot having a longitudinal axis and a distal end flared radially outwardly to form an enlarged, hollow distal flange, the flange having a generally planar shape and comprising a distal facing closure wall having an opening and providing a sealing surface for the female connector rim, the flange further comprising a proximal surface connected with an annular side wall to the closure wall adapted to provide stability to the closure wall and to maintain the generally planar shape of the flange when the resilient boot is compressed;
  wherein the configuration of the distal flange enables the distal flange and the closure wall to remain substantially planar and perpendicular to the boot's longitudinal axis further enabling the boot to be compressed substantially axially and uniformly while a flat sealing surface continues to be presented to the female connector;
  wherein the boot comprises a resilient mounting lip for receipt in the mounting groove to thereby hold the boot in position on the post; and
  a second engagement device mounted to the body, the second engagement device adapted to interact with the first engagement device of the female connector to secure the female and male connectors together in an engaged configuration.

11. A self-sealing male connector for connecting to a female connector having a generally tubular barrel with external thread portions and a proximal rim, the self-sealing male connector comprising:

a body having a proximal end and a distal end, the proximal end having a fluid flow opening and the distal end being configured as an elongate post extending distally of a shoulder and having a proximal post portion that is cylindrical in form and a distal post portion that is tapered to a smaller-diameter distal post tip, the proximal post portion being formed with adjacent first and second grooves, and wherein an internal lumen communicates between the proximal and distal ends;

a resilient boot mounted in covering relationship about the post in the second groove, the boot being configured so as to cover the distal end of the post when the boot is in an at-rest condition, thereby restricting fluid within the internal lumen from escaping, the boot having a longitudinal axis and a distal end flared radially outwardly to form an enlarged, hollow distal flange, the flange having a generally planar shape and comprising a distal facing closure wall having a diametrical slit and providing a sealing surface for the female connector rim, the flange further comprising a proximal surface connected with an annular side wall to the closure wall adapted to provide stability to the closure wall and to maintain the generally planar shape of the flange when the resilient boot is compressed;

wherein the configuration of the distal flange enables the distal flange and the closure wall to remain substantially planar and perpendicular to the boot's longitudinal axis further enabling the boot to be compressed substantially axially and uniformly while a flat sealing surface continues to be presented to the female connector; and a male thread hub having internal threads and mounted circumferentially about the boot and the post in the first groove such that there exists nothing between the hub and boot at the distal end, whereby engagement of the hub with the female connector along the hub's internal threads and the female connector's thread portions serves to bring the distal end of the boot into contact with the female connector to thereby compress the boot, causing the post tip to protrude through the slit, and allowing fluid communication between the self-sealing male connector and the female connector through the internal lumen.

* * * * *

UNITED STATES PATENT AND TRADEMARK OFFICE
CERTIFICATE OF CORRECTION

| | | |
|---|---|---|
| PATENT NO. | : 7,040,598 B2 | Page 1 of 1 |
| APPLICATION NO. | : 10/438702 | |
| DATED | : May 9, 2006 | |
| INVENTOR(S) | : John Raybuck | |

It is certified that error appears in the above-identified patent and that said Letters Patent is hereby corrected as shown below:

Title Page, (57) ABSTRACT,
Line 13, delete "with eh" and insert --with the--.
Line 19, delete "passage within disconnected" and insert --passage when disconnected--.

Column 23,
Line 4, delete "has".

Signed and Sealed this

Nineteenth Day of December, 2006

JON W. DUDAS
*Director of the United States Patent and Trademark Office*